United States Patent
Crameri et al.

(10) Patent No.: US 6,479,652 B1
(45) Date of Patent: Nov. 12, 2002

(54) OLIGONUCLEOTIDE MEDIATED NUCLEIC ACID RECOMBINATION

(75) Inventors: Andreas Crameri, Reinach (CH); Willem P. C. Stemmer, Los Gatos, CA (US); Jeremy Minshull, Menlo Park, CA (US); Steven H. Bass, Hillsborough, CA (US); Mark Welch, Fremont, CA (US); Jon E. Ness, Sunnyvale, CA (US); Claes Gustafsson, Belmont, CA (US); Phillip A. Patten, Mountain View, CA (US)

(73) Assignee: Maxygen, Inc., Redwood City, CA (US)

( * ) Notice: Subject to any disclaimer, the term of this patent is extended or adjusted under 35 U.S.C. 154(b) by 0 days.

(21) Appl. No.: 09/626,595

(22) Filed: Jul. 27, 2000

Related U.S. Application Data

(62) Division of application No. 09/408,392, filed on Sep. 28, 1999.
(60) Provisional application No. 60/118,813, filed on Feb. 5, 1999, provisional application No. 60/141,049, filed on Jun. 24, 1999, provisional application No. 60/116,447, filed on Jan. 19, 1999, and provisional application No. 60/118,854, filed on Feb. 5, 1999.

(51) Int. Cl.$^7$ .................. C07H 21/02; C07H 21/04; C12N 15/00; C12P 19/34; C12Q 1/68
(52) U.S. Cl. .................. 536/23.1; 536/24.3; 435/440; 435/91.2; 435/6
(58) Field of Search .................. 536/23.1, 24.3; 435/6, 91.2, 440; 935/76, 77, 7 D

(56) References Cited

U.S. PATENT DOCUMENTS

| | | |
|---|---|---|
| 4,959,312 A | 9/1990 | Sirokin |
| 4,994,379 A | 2/1991 | Chang |
| 5,023,171 A | 6/1991 | Ho et al. |
| 5,043,272 A * | 8/1991 | Hartley et al. |
| 5,066,584 A * | 11/1991 | Gyllensten et al. |
| 5,264,563 A | 11/1993 | Huse |
| 5,319,308 A | 6/1994 | Dechene |
| 5,408,181 A | 4/1995 | Dechene |
| 5,447,839 A | 9/1995 | Manos et al. |
| 5,506,793 A | 4/1996 | Stemmer |
| 5,512,463 A | 4/1996 | Stemmer |
| 5,514,588 A | 5/1996 | Varadaraj |
| 5,519,319 A | 5/1996 | Smith |
| 5,521,077 A | 5/1996 | Kholsa et al. |
| 5,565,350 A | 10/1996 | Kmiec |
| 5,580,730 A | 12/1996 | Okamoto |
| 5,603,793 A | 2/1997 | Yoshida et al. |
| 5,605,793 A | 2/1997 | Stemmer |
| 5,612,205 A | 3/1997 | Kay et al. |
| 5,650,722 A | 7/1997 | Smith |

(List continued on next page.)

FOREIGN PATENT DOCUMENTS

| | | |
|---|---|---|
| EP | 0911396 A2 | 4/1999 |
| EP | 0911396 A3 | 5/1999 |
| EP | 0934999 A1 | 8/1999 |
| WO | WO91/06643 A1 | 5/1991 |
| WO | WO92/06176 | 4/1992 |
| WO | WO95/15972 | 6/1995 |
| WO | WO95/22625 | 8/1995 |
| WO | WO96/16073 A3 | 5/1996 |
| WO | WO96/16073 A2 | 5/1996 |
| WO | WO96/33207 | 10/1996 |
| WO | WO97/07205 | 2/1997 |
| WO | WO97/20078 | 6/1997 |
| WO | WO97/25410 | 7/1997 |
| WO | WO97/33957 | 9/1997 |
| WO | WO97/35957 | 10/1997 |

(List continued on next page.)

OTHER PUBLICATIONS

Zoller M., Current Opinions in Biotechnology 3: 348–354 (1992).*

Dahiyat et al., "Automated design of the surface positions of protein helices" *Protein Science* (1997) 6:1333–1337.

Dahiyat and Mayo "De Novo Protein Design: Fully Automated Sequence Selection" *Science* (1997) vol. 278 pp. 82–87.

Dahiyat et al., "De Novo Protein Design: Towards Fully Automated Sequence Selection" *J. Mol. Biol.* (1997) 273:789–796.

Dahiyat and Mayo "Probing the role of packing specificity in protein design" *Proc. Matl. Acad. Sci. U.S.A.* vol. 94 pp. 10172–10177.

Gordon and Mayo "Branch–and–Terminate: a combinatorial optimization algorithm for protein design" *Structure* (1999) 7:1089–1098.

Gordon et al., "Energy functions for protein design" *Current Opinion in Structural Biology* (1999) 9:509–513.

Gordon and Mayo "Radical Performance Enhancements for Combinatorial Optimization Algorithms Based on the Dead– End Elimination Theorem" *Journal of Computational Chemistry* vol. 19. No. 13, 1505–1514.

Haney et al., "Structural Basis for Thermostability and Identification of Potential Active Site Residues for Adenylate Kinases From the Archaeal Genus Methanococcus" *Proteins* (1997) 28:117–130.

Malakauskas and Mayo "Design, structure and stability of a hyperthermophilic protein variant" *Nature Structural Biology* (1998) vol. 5, No. 6, 470–475.

(List continued on next page.)

*Primary Examiner*—Ethan C. Whisenant
(74) *Attorney, Agent, or Firm*—Sharon Fujita; Norman J. Kruse; Quine Intellectual Property Law Group, P.C.

(57) ABSTRACT

Methods of recombining nucleic acids, including homologous nucleic acids, are provided. Families of gene shuffling oligonucleotides and their use in recombination procedures, as well as polymerase and ligase mediated recombination methods are also provided.

94 Claims, 3 Drawing Sheets

U.S. PATENT DOCUMENTS

| | | |
|---|---|---|
| 5,675,253 A | 10/1997 | Smith |
| 5,717,085 A | 2/1998 | Lyttle et al. |
| 5,760,012 A | 6/1998 | Kmiec et al. |
| 5,763,239 A | 6/1998 | Short et al. |
| 5,789,228 A | 8/1998 | Lam et al. |
| 5,789,577 A | 8/1998 | Geysen |
| 5,811,238 A | 9/1998 | Stemmer et al. |
| 5,814,473 A | 9/1998 | Warren et al. |
| 5,824,469 A | 10/1998 | Short |
| 5,830,696 A | 11/1998 | Short |
| 5,830,721 A | 11/1998 | Stemmer et al. |
| 5,834,252 A | 11/1998 | Stemmer et al. |
| 5,837,458 A | 11/1998 | Minushull et al. |
| 5,866,363 A | 2/1999 | Pieczenik |
| 5,869,644 A | 2/1999 | Shortle et al. |
| 5,876,997 A | 3/1999 | Kretz |
| 5,912,119 A | 6/1999 | Radman et al. |
| 5,925,749 A | 7/1999 | Mathur et al. |
| 5,928,905 A | 7/1999 | Stemmer et al. |
| 5,939,250 A | 8/1999 | Short |
| 5,939,300 A | 8/1999 | Robertson et al. |
| 5,942,430 A | 8/1999 | Robertson et al. |
| 5,948,666 A | 9/1999 | Callen et al. |
| 5,958,672 A | 9/1999 | Short |
| 5,958,751 A | 9/1999 | Murphy et al. |
| 5,962,258 A | 10/1999 | Mathur et al. |
| 5,962,283 A | 10/1999 | Warren et al. |
| 5,965,408 A | 10/1999 | Short |
| 5,985,646 A | 11/1999 | Murphy et al. |
| 6,001,574 A | 12/1999 | Short et al. |
| 6,004,788 A | 12/1999 | Short |
| 6,030,779 A | 2/2000 | Short |
| 6,054,267 A | 4/2000 | Short |
| 6,096,548 A | 8/2000 | Stemmer |
| 6,117,679 A | 9/2000 | Stemmer |
| 6,132,970 A | 10/2000 | Stemmer |
| 6,153,410 A | 11/2000 | Arnold et al. |
| 6,159,690 A | 12/2000 | Borrebaeck et al. |

FOREIGN PATENT DOCUMENTS

| | | |
|---|---|---|
| WO | WO97/35966 | 10/1997 |
| WO | WO97/44361 | 11/1997 |
| WO | WO97/48416 | 12/1997 |
| WO | WO97/48717 | 12/1997 |
| WO | WO97/48794 | 12/1997 |
| WO | WO98/00526 | 1/1998 |
| WO | WO98/01581 | 1/1998 |
| WO | WO98/13485 | 4/1998 |
| WO | WO98/13487 | 4/1998 |
| WO | WO98/24230 | 6/1998 |
| WO | WO98/24799 | 6/1998 |
| WO | WO98/28416 | 7/1998 |
| WO | WO98/31837 | 7/1998 |
| WO | WO98/36080 | 8/1998 |
| WO | WO98/41622 | 9/1998 |
| WO | WO98/41623 | 9/1998 |
| WO | WO98/41653 | 9/1998 |
| WO | WO98/42832 | 10/1998 |
| WO | WO98/48034 | 10/1998 |
| WO | WO98/49350 | 11/1998 |
| WO | WO98/58085 | 12/1998 |
| WO | WO99/07837 | 2/1999 |
| WO | WO99/08539 | 2/1999 |
| WO | WO99/10472 | 3/1999 |
| WO | WO99/10539 | 3/1999 |
| WO | WO99/19518 | 4/1999 |
| WO | WO99/21979 | 5/1999 |
| WO | WO99/23107 | 5/1999 |
| WO | WO99/23236 | 5/1999 |
| WO | WO99/41368 | 8/1999 |
| WO | WO99/41369 | 8/1999 |
| WO | WO99/41383 | 8/1999 |
| WO | WO99/41402 | 8/1999 |
| WO | WO99/45154 | 9/1999 |
| WO | WO99/57128 | 11/1999 |
| WO | WO99/65927 | 12/1999 |
| WO | WO00/00632 | 1/2000 |
| WO | WO00/53744 | 1/2000 |
| WO | WO00/37684 | 6/2000 |
| WO | WO00/42560 | 7/2000 |
| WO | WO00/42561 | 7/2000 |
| WO | WO00/58517 | 10/2000 |

OTHER PUBLICATIONS

Pollock et al., "Coevolving Protein Residues: Maximum Likelihood Identification and Relationship to Structure" *J. Mol. Biol.* (1999) 287:187–189.

Street and Mayo "Computational protein design" *Structure* (1999) 7:R105–R109.

Street and Mayo "Intrinsic B–sheet propensities result from van der Waals interactions between side chains and local backbone" *Proc. Natl. Acad. Sci. U.S.A.* (1999) vol. 96 pp. 9074–9076.

Street and Mayo "Pairwise calculation of protein solvent–accessible surface areas" *Folding & Design* (1998) 3:253–258.

Strop and Mayo "Rubredoxin Variant Folds without Iron" *J. American Chem. Soc.* (1999) vol. 121 No. 11 pp. 2341–2345.

Wollenberg and Atchley "Separation of phylogenetic and functional associations in biological sequences by using the parametric bootstrap" *PNSA* vol. 97, No. 7, pp. 3288–3291.

Stemmer (1994) DNA shuffling by random fragmentation and reassembly: In vitro recombination for molecular evolution *Proc. Natl. Acad. Sci. USA* vol. 91, pp. 10747–10751.

Venkatasubramanian et al., (1995) "Evolutionary Design of Molecules with Desired Properties Using the Genetic Algorithm" *J. Chem. Inf. Comput. Sci.* vol. 35 pp. 188–195.

Singh et al. (1996) "Application of Genetic Algorithms to Combinatorial Synthesis: A Computational Approach to Lead Identification and Lead Optimization" *J. Chem. Inf. Comput. Sci* vol. 118 pp 1669–1676.

Harayama, Shigeaki, (1998) "Artificial evolution by DNA shuffling" *Tibtech* vol. 16 pp. 76–82.

Zhang, Ching (1994) "A Genetic Algorithm for Molecular Sequence Comparison" *Proceedings of the International Conference on Systems, Man, and Cybernetics* pp 1926–1931.

Stemmer et al., Single–step assembly of a gene and entire plasmid for large numbers of oligodeoxyribonucleotides *Gene* 164 (1995) 49–53.

Crameri & Stemmer "1020–Fold aptamer library amplification without gel purification" *Nucleic Acid Research* (1993) vol. 21 No. 18 p. 4110.

Feng & Doolittle, *J. Mol. Evol.* 35:351–360 (1987).

Higgins & Sharp, *CABIOS* 5:151–153 (1989).

Sun (1999) "Modeling DNA Shuffling" *Journal of Computational Biology* 6(1):77–90.

Alexeev and Yoon (1998) *Nature Biotechnology* 1343:1346.*

Bartlett (1998) *Nature Biotechnology* 16:1312.*

Botstein & Shortle (1985) "Strategies and applications of in vitro mutagenesis" *Science* 229:1193–1201.*

Carter (1986) "Site–directed mutagenesis" *Biochem J.* 237:1–7.*

Chang, C., et al. (1999) "Evolution of a cytokine using DNA family shuffling," *Nature Biotechnolgy* 17:793–797.*

Chee et al. (1996) "Accessing Genetic Information with High–Density DNA Arrays" *Science* 274:610–614.*

Cole–Strauss et al. (1996) *Science* 1386–1389.*

Christians, F.C. et al., (1999) "Directed evolution of thymidine kinase for AZT phosphoylation using DNA family shuffling," *Nature Biotechology* 17:259–264.*

Crameri et al., (1993) "10(20)–Fold aptamer library amplification without gel purification," *Nuc. Acids Res.* 21(18):4410.*

Crameri, A. et al., (1997) "Molecular evolution of an arsenate detoxification pathway by DNA shuffling." *Nature Biotechnology* 14:436–438.*

Crameri, A. et al., (1996) "Improved green fluorescent protein by molecular evolution using DNA shuffling." *Nature Biotechnology* 14:315–319.*

Dale et al. (1996) "Oligonucleotide–directed random mutagenesis using the phosphorothioate method" *Methods Mol Biol.* 57:369–74.*

Fodor (1997) "Genes, Chips and the Human Genome" *FASEB Journal.* 11:121–121.*

Fodor (1997) "Massively Parallel Genomics" *Science.* 277:393–395.*

Fodor et al. (1991) *Science*, 251:767–777.*

Gates, C.M. et al., (1996) "Affinity selective isolation of ligands from peptide libraries through display on a lac repressor 'headpiece dimer". *Journal of Molecular Biology* 255:373–386.*

Hill et al. (1993) *PNAS* 90:5167.*

Karlin & Altschul (1993) *Proc. Nat'l. Acad. Sci. USA* 90:5873–5787.*

Kren et al. (1997) *Hepatology* 25(6):146201468.*

Kren et al. (1998) *Nature Medicine* 4(3):285–290.*

Kunkel (1987) "The efficiency of olignucleotide directed mutagenesis" *Nucleic Acids & Molecular Biology* (1987).*

Minshull, J., Stemmer, W.P.C. (1999) "Protein evolution by molecular breeding." *Current Opinion in Chemical Biology* 3:284–290.

Ness, J. et al., (1999) "DNA shuffling of subgenominc sequences of subtilisin." *Nature Biotechnology* 17:893–896.

Patthy (1999) *Current Opinions in Structural Biology* 1:351–361.

Patthy (1994) *Current Opinions in Structural Biology* 4:383–392.

Porter et al. (1997) *Nucleic Acids Research* 25(8):1611–1617.

Stemmer, W.P.C. (1995) "The Evolution of Molecular Computation." *Science* 270:1510.

Stemmer, W.P.C. (1996) "Sexual PCR and Assembly PCR." In: *The Encyclopedia of Molecular Biology*. VCH Publishers, New York. pp. 447–457.

Stemmer, W.P.C. & Soong, N.W. (1999) "Molecular breeding of viruses for targeting and other clinical properties." *Tumor Targeting* 4:59–62.

Strauss (1998) *Nature Medicine* 4:274–275.

Von der Osten et al., *J. Biotechnol.* 28:55–68 (1993).

Xiang et al (1997) *J. Mol. Med.* 75:829–835.

Yoon et al. (1996) *PNAS* 93:2071–2076.

Young et al. (1997) *Protein Science* 6:1228–1236.

Zhang, J. et al., (1997) "Directed evolution of an effective fucosidase from a galactosidase by DNA shuffling and screening." *Proceedings of the National Academy of Sciences, USA* 94:4504–4509.

Alberts et al. "Rocombinant DNA Technology." In: Molecular Biology of Cell. New York: Garland Publishing, Inc., 1994, pp. 291–312.

Kaczorowski et al. "Co–operaticity of hexmer ligationl." *Gene.* 1996, vol. 179, No. 1 pages 189–193.

Mintz et al. "EHDI–An IH–domain–containing protein with a specific expression pattern." *Genomics.* Jul. 01, 1999, vol. 59, No. 1 pp. 66–76.

Giver and Arnold "Combinatorial protein design by in vitro recombination" *Current Opinion in Chemical Biology* (1998) 2:335–338.

Pattern et al., "Applications of DNA shuffling to pharamceuticals and vaccines" *Current Opinion in Chemical Biology* (1997) 8:724–733.

Sun, Fengzhu, "Modeling DNA Shuffling" *Proceedings of the Second Annual International Conference of Computational Molecular Biology* (1998) 251–257.

Zhao et al., "Molecular evolution by staggered extention process (StEP) in vitro recombination" *Nature Biotechnology* vol. 16 (1998) pp. 258–261.

Altschul et al., *J. Mol. Biol.* 215:403–410 (1999).

Carter (1987) "Improved oligonucleotide–directed mutagenesis using M13 vectors." *Methods in Enzymol.* 154:382–403.

Carter et al. (1985) "Improved oligonucleotides site directed mutagenesis using M13 vectors" *Nucleic Acids Res.* 13, 4431–4443.

Crameri et al. (1996), "Construction And Evolution Of Antibody–Phage Libraries By DNA Shuffling" *Nature Medicine* 2(1):100–103.

Crameri et al. (1998) *Bio techniques* 18(2): 194–196.

Crameri et al. (1998) *Nature* 391: 288–291.

Kayushin, A. L. et al., (1996) *Nucleic Acids Res.*, 24, 3748–3755.

Ling et al. (1997) "Approaches to DNA mutagenesis: an overview." *Anal Biochem.* Dec. 15;254(2):157–78.

Nakamaye & Eckstein (1986) "Inhibition of restriction endonuclease Nci I cleavage by phosphorothioate groups and its application to oligonucleotide–directed mutagenesis." *Nucleic Acids Res.* 14: 9679–9698.

Needleman & Wunsch, *J. Mol. Biol.* 48:443 (1970).

Pearson & Lipman, *Proc. Nat'l. Acad. Sci. USA* 85:2444 (1988).

Sayers et al. (1988) "5'–3' Strand specific cleavage of phosphorothioate–containing DNA by reaction with restriction endonucleases in the presence of ethidium bromide" *Nucleic Acids Res.* 16:803–814.

Sayers et al. (1988). "Y–T Exonucleases in phosphorothioate–based oligonucleotide–directed mutagenesis." *Nucleic Acids Res.* 16:791–802.

Smith & Waterman, *Adv. Appl. Math.* 2:482 (1981).

Smith (1985) "In vitro mutagenesis" *Ann. Rev. Genet.* 19:423–462.

Stemmer (1995) *Biotechnology* 13:549–553.

Stemmer et al. (1994) "Rapid Evolution of a Protein" *Nature* 370:389–391.

Taylor et al. (1985) "The rapid generation of oligonucleotide–directed mutations at high frequency using phosphorothioate–modified DNA" *Nucleic Acids Res.* 13:8765–8787.

Taylor et al. (1985) "The use of phosphorothioate–modified DNA in restriction enzyme reactions to prepare nicked DNA." *Nucleic Acids Res.* 13:8749–8764.

Virnekäs, B., et al., (1994) *Nucleic Acids Res.*, 22, 5600–5607.

Wells (1986) "Importance of hydrogen bond formation in stabilizing the transition state of subtilisin." *Trans. R. Soc. Lond.* A317, 415–423.

Mehling, et al. "Nucleotide sequences 16S ribosomal DNA: towards a specific identification system for streptomycetes using PCR" *Microbiology* (1995) 141:2139–2147.

Muerhoff, et al. "Identification of conserved nucleotide sequences within the GB virus C 5'–untranslated region: Design of PCR primers for detection of viral RNA" *Journal of Virological Methods* (1996) 62:55–62.

U.S. patent application Ser. No. 09/408,392, Crameri et al., filed Sep. 28, 1999.

U.S. patent application Ser. No. 09/408,393, Welch et al., filed Sep. 29, 1999.

U.S. patent application Ser. No. 09/416,375, Selifono et al., filed Oct. 10, 1999.

U.S. patent application Ser. No. 09/484,850, Cameri et al., filed Jan. 18, 2000.

U.S. patent application Ser. No. 09/539,486, Selifono et al., filed Mar. 30, 2000.

U.S. patent application Ser. No. 09/618,579, Selifono et al., filed Jul. 18, 2000.

U.S. patent application Ser. No. 09/626,595, Cameri et al., filed Jul. 27, 2000.

U.S. patent application Ser. No. 09/626,601, Cameri et al., filed Jul. 27, 2000.

U.S. patent application Ser. No. 09/626,929, Cameri et al., filed Jul. 27, 2000.

U.S. patent application Ser. No. 09/626,930, Cameri et al., filed Jul. 27, 2000.

U.S. patent application Ser. No. 09/626,588, Cameri et al., filed Jul. 27, 2000.

U.S. patent application Ser. No. 09/694,864, Cameri et al., filed Jul. 27, 2000.

U.S. patent application Ser. No. 09/718,682, Selifono et al., filed Nov. 21, 2000.

U.S. patent application Ser. No. 09/718,765, Selifono et al., filed Nov. 21, 2000.

U.S. patent application Ser. No. 09/718,849, Selofinov et al., filed Nov. 21, 2000.

U.S. patent application Ser. No. 09/721,365, Selifonov et al., filed Nov. 21, 2000.

U.S. patent application Ser. No. 09/721,395, Selifonov et al., filed Nov. 21, 2000.

U.S. patent application Ser. No. 09/721,396, Selifonov et al., filed Nov. 21, 2000.

U.S. patent application Ser. No. 09/721,598, Selifonov et al., filed Nov. 21, 2000.

U.S. patent application Ser. No. 09/721,601, Cameri et al., filed Nov. 21, 2000.

Arkin "Optimizing Nucleotide Mixtures to Encode Specific Subsets of Smino Acids for Semi–Random Mutagenesis." Biotechnology (N Y). Mar. 1992;10(3):297–300.

Arkin "An algorithm for protein engineering: Simulations of recursive ensemble mutagenesis." Proc Natl Acad Sci USA. Aug. 15 1992;89(16):7811–5.

Boehnke et al. "Statistical Methods for Multipoint Radation Hybrid Mapping." *Am. J. Hum. Genet.* 49:1174–1188 (1991).

Brunner & Bujard "Promoter recognition and promoter strength in the *Eschichia coli*." *EMBO J.* 6:3139–3144 (1987).

Delagrave "Searching Sequence Space to Engineer Proteins: Exponential Ensemble Mutagenesis." Biotechnology (N Y). Dec. 1993; 11 (13):1548–52.

Delagrave "Recursive ensemble mutagenesis." Protein Eng. Apr. 1993;6(3):327–31.

Delagrave "Context dependence of phenotype prediction and diversity in combinatorial mutagenesis." Protein Eng. Mar. 1995;8(3):237–42.

Egea Biosciences, Inc. "Pathway to the Proteome".

Feng et al. "Progressive Sequence Alignment as a Prerequisite to Correct Phytogenetic Trees." *J. Mol. Evol.* 35:351–360 (1987).

Goldman "An Algprithmically Optimized Combinatorial Library Screened by Digital Imaging Spectroscopy." Biotechnology (N Y). Dec. 1992;10(12):1557–61.

Higgins et al. "Fast and Seneitive Multiple Sequence Alignment on a Microcomputer." *CABIOS* 5:151–153 (1989).

Irvine et al. "Systematic Evolution of Ligands by Exponential Enrichment with Integrated Optimization by Non–linear Analysis." *J. Mol. Biol.* 222:739–761 (1991).

Jonsson et al. "Quantitative sequence–activity models (QSAM)– tools for sequence design." *Nucleic Acids Res.* 21:733–739 (1993).

Kelly et al. "A Test of the Markovian Model of DNA Evolution." *Biometrice* 50(3):653–664 (1994).

Knaus And Bujard "$P_L$ of coliphage lambda: an alternative solution for an efficient promoter." *EMBO J.*7:2912–2923 (1998).

Lander And Waterman "Genomic Mapping by Fingerprinting Random Clones: A Mathematical Analysis." *Genomics* 2:231–239 (1998).

Lanzer and Bujard "Promoters largely determine the efficiency for repressor action." *Proc. Natl. Acad. Sci. USA*85:8973–8977 (1988).

Robles "Hydropathy and Molar Volume Constraints on Combinatorial Mutants of the Photosynthetic Reaction Center." J Mol Biol. Jul. 5, 1993;232(1):242–52.

Sun et al. "A Mathematical Analysis of in vitro Molecular Selection–Amplification." *J. Mol. Biol.* 258:650–660 (1996).

Sun "Modeling DNA Shuffling." *J. of Computational Biology* 6(1):77–90 (1999).

Whipple et al. "Application od Genetic Algorithms to Combinatorial Synthesis: A Computational Approach to Lead Identification and Lead Optimization." *J. AM. Chem Soc.* 118:1669–1676 (1996).

Yokomori et al. "A Similarity measure for DNA sequence analysis based on locality." *Genome Inf. Ser.* 4:283–292 (1993).

Youvan "Imaging Sequence Space." Nature. May 5, 1994;369(6475):79–80.

Dewey et al. (1998) "Non–equilibrum Thermodynamics of Molecular Evolution." *J. Theor Biol.*193:593–599.

Morchio et al. (1997) "Simulation of Protein Evolution: Evidence for a Non–linear Aminoacidic Substitution Rate." *Riv Biol* 83–94.

* cited by examiner

SEQUENCE LISTING

<160> NUMBER OF SEQ ID NOS: 26

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Bridging
      oligonucleotides

<400> SEQUENCE: 1
caaatactgg ccggaactga aaggttctgc tttcgacggt                           40

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Bridging
      oligonucleotides

<400> SEQUENCE: 2
gtcgtgttct gcagccgctg ggtctgcacc acacctacat                           40

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Bridging
      oligonucleotides

<400> SEQUENCE: 3
tcgttactgg cgtatcggtg acatgaccca gggtctgggt                           40

```
<210> SEQ ID NO 4
<211> LENGTH: 56
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
tggtcgttat ttaaatatca aagccttcta gtatcttccg gcgctaattt atatgc        56

<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
cggcgctaat ttatatgcga gtggtagtgg tccaacacaa tcatttacag caca          54

<210> SEQ ID NO 6
<211> LENGTH: 59
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
ctaattatgt attaaatggt ttgagtggtg ctaggaccac cattactttc cctaatatt     59

<210> SEQ ID NO 7
<211> LENGTH: 59
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
ctttccctaa tattggtggt cttcccgtct accacaactc aacattgcat tttgcgagg     59

<210> SEQ ID NO 8
<211> LENGTH: 53
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
aggattaatt atagaggtgg agtgtcatct agccgcatag gtcaagctaa tct           53

<210> SEQ ID NO 9
<211> LENGTH: 59
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
ctaatcttaa tcaaaacttt aacatttcca cacttttcaa tcctttacaa acaccgttt     59
```

<210> SEQ ID NO 10
<211> LENGTH: 56
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
tttattagaa gttggctaga ttctggtaca gatcgggaag gcgttgccac ctctac      56

<210> SEQ ID NO 11
<211> LENGTH: 49
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
tgccacctct acaaactggc aatcaggagc ctttgagaca actttatta      49

<210> SEQ ID NO 12
<211> LENGTH: 57
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
acaactttat tacgatttag catttttca gctcgtggta attcgaactt tttccca      57

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13
tccgtaatat ttctggtgtt gttgggacta ttagcaacgc agatttagca agacctctac      60

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14
actttaatga aataagagat ataggaacga cagcagtcgc tagccttgta acagtgcata      60

<210> SEQ ID NO 15
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15
taatatctat gacactcatg aaaatggtac tatgattcat ttagcgccaa atgactatac      60

```
<210> SEQ ID NO 16
<211> LENGTH: 59
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 16
tatacaggat ttaccgtatc tccaatacat gccactcaag taaataatca aattcgaac        59

<210> SEQ ID NO 17
<211> LENGTH: 59
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 17
caaattcgaa cgtttatttc gaaaaaatat ggtaatcagg gtgattcctt gagatttga        59

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 18
agatttgagc taagcaaccc aacggctcga tacacactta gagggaatgg aaatagttac        60

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 19
agagtatctt caataggaag ttccacaatt cgagttacta                             40

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 20
ctgcaaatgt taatactacc acaaataatg atggagtact tgataatgga gctcgttttt       60

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 21
tatcggtaat gtagtggcaa gtgctaatac taatgtacca ttagatatac aagtgacatt       60
```

```
-continued

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 22
atacaagtga catttaacgg caatccacaa tttgagctta tgaatattat gtttgttcca        60

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 23
atgaataatg tattgaata                                                     19

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 24
ttaataaagt ggtggaagat t                                                  21

<210> SEQ ID NO 25
<211> LENGTH: 12
<212> TYPE: DNA
<213> ORGANISM: Homo sapiens
<220> FEATURE:
<221> NAME/KEY: CDS
<222> LOCATION: (1)..(12)

<400> SEQUENCE: 25 tgg ggg tcc aga                                                          12
Trp Gly Ser Arg
  1

<210> SEQ ID NO 26
<211> LENGTH: 4
<212> TYPE: PRT
<213> ORGANISM: Homo sapiens

<400> SEQUENCE: 26

Trp Gly Ser Arg
  1
```

OLIGONUCLEOTIDE MEDIATED NUCLEIC ACID RECOMBINATION

CROSS REFERENCE TO RELATED APPLICATIONS

This application is a divisional of and claims the benefit of U.S. Application Ser. No. 09/408,392 filed Sep. 28, 1999 which is a non-provisional application of 60/118,813 filed Feb. 5, 1999 and a non-provisional application of 60/141, 049 filed Jun. 24, 1999 and a non-provisional application of U.S. Ser. No. 60/116,447 filed Jan. 19, 1999 and a non-provisional application of U.S. Ser. No. 60/118,854 filed Feb. 5, 1999. This application also claims priority to U.S. Ser. No. 09/408,393 filed Sep. 28, 1999. The disclosures of each of these prior applications are incorporated by reference for all purposes.

BACKGROUND OF THE INVENTION

DNA shuffling has provided a paradigm shift in recombinant nucleic acid generation, manipulation and selection. The inventors and their co-workers have developed fast artificial evolution methodologies for generating improved industrial, agricultural, and therapeutic genes and encoded proteins. These methods, and related compositions and apparatus for practicing these methods represent a pioneering body of work by the inventors and their co-workers.

A number of publications by the inventors and their co-workers describe DNA shuffling. For example, Stemmer et al. (1994) "Rapid Evolution of a Protein" Nature 370:389–391; Stemmer (1994) "DNA Shuffling by Random Fragmentation and Reassembly: in vitro Recombination for Molecular Evolution," Proc. Natl. Acad. USA 91:10747–10751; Stemmer U.S. Pat. No. 5,603,793 METHODS FOR IN VITRO RECOMBINATION; Stemmer et al. U.S. Pat. No. 5,830,721 DNA MUTAGENESIS BY RANDOM FRAGMENTATION AND REASSEMBLY; Stemmer et al., U.S. Pat. No. 5,811,238 METHODS FOR GENERATING POLYNUCLEOTIDES HAVING DESIRED CHARACTERISTICS BY ITERATIVE SELECTION AND RECOMBINATION describe, e.g., in vitro nucleic acid, DNA and protein shuffling in a variety of formats, e.g., by repeated cycles of mutagenesis, shuffling and selection, as well as methods of generating libraries of displayed peptides and antibodies.

Applications of DNA shuffling technology have also been developed by the inventors and their co-workers. In addition to the publications noted above, Minshull et al., U.S. Pat. No. 5,837,458 METHODS AND COMPOSITIONS FOR CELLULAR AND METABOLIC ENGINEERING provides, e.g., for the evolution of metabolic pathways and the enhancement of bioprocessing through recursive shuffling techniques. Crameri et al. (1996), "Construction And Evolution Of Antibody-Phage Libraries By DNA Shuffling" Nature Medicine 2(1):100–103 describe, e.g., antibody shuffling for antibody phage libraries. Additional details regarding DNA Shuffling can be found in WO95/22625, WO97/20078, WO96/33207, WO97/33957, WO98/27230, WO97/35966, WO98/31837, WO98/13487, WO98/13485 and WO989/42832, as well as a number of other publications by the inventors and their co-workers.

A number of the publications of the inventors and their co-workers, as well as other investigators in the art also describe techniques which facilitate DNA shuffling, e.g., by providing for reassembly of genes from small fragments, or even oligonucleotides. For example, in addition to the publications noted above, Stemmer et al. (1998) U.S. Pat. No. 5,834,252 END COMPLEMENTARY POLYMERASE REACTION describe processes for amplifying and detecting a target sequence (e.g., in a mixture of nucleic acids), as well as for assembling large polynucleotides from nucleic acid fragments.

Review of the foregoing publications reveals that forced evolution by gene shuffling is an important new technique with many practical and powerful applications. Thus, new techniques which facilitate gene shuffling are highly desirable. The present invention provides significant new gene shuffling protocols, as well as many other features which will be apparent upon complete review of this disclosure.

SUMMARY OF THE INVENTION

The invention provides oligonucleotide assisted shuffling of nucleic acids. These oligonucleotide assisted approaches particularly facilitate family shuffling procedures, providing substantially simplified shuffling protocols which can be used to produce family shuffled nucleic acids without isolating or cloning full-length homologous nucleic acids. Furthermore, the oligonucleotide assisted approaches herein can even be extended to shuffling non-homologous nucleic acids, thereby accessing greater sequence space in resulting recombinant molecules and, thus, greater molecular diversity. The techniques can also be combined with classical DNA shuffling protocols, such as DNAse-mediated methods. to increase the versatility and throughput of these methods.

Several methods which are applicable to family shuffling procedures are provided. In one aspect of these methods, sets of overlapping family gene shuffling oligonucleotides are hybridized and elongated, providing a population of recombined nucleic acids, which can be selected for a desired trait or property. Typically, the set of overlapping family shuffling gene oligonucleotides include a plurality of oligonucleotide member types which have consensus region subsequences derived from a plurality of homologous target nucleic acids. The oligo sets optionally provide other distinguishing features, including crossover capability, codon-variation or selection, and the like.

The population of recombined nucleic acids can be denatured and reannealed, providing denatured recombined nucleic acids which can then be reannealed. The resulting recombinant nucleic acids can also be selected. Any or all of these steps can be repeated reiteratively, providing for multiple recombination and selection events to produce a nucleic acid with a desired trait or property.

In a related aspect, methods for introducing nucleic acid family diversity during nucleic acid recombination are performed by providing a composition having at least one set of fragmented nucleic acids which includes a population of family gene shuffling oligonucleotides and recombining at least one of the fragmented nucleic acids with at least one of the family gene shuffling oligonucleotides. A recombinant nucleic acid having a nucleic acid subsequence corresponding to the at least one family gene shuffling oligonucleotide is then regenerated, typically to encode a full-length molecule (e.g., a full-length protein).

Typically, family gene shuffling oligonucleotides are provided by aligning homologous nucleic acid sequences to select conserved regions of sequence identity and regions of sequence diversity. A plurality of family gene shuffling oligonucleotides are synthesized (serially or in parallel) which correspond to at least one region of sequence diversity. In contrast, sets of fragments are provided by cleaving one or more homologous nucleic acids (e.g., with a DNase), or by synthesizing a set of oligonucleotides corresponding to a plurality of regions of at least one nucleic acid (typically oligonucleotides corresponding to a full-length nucleic acid are provided as members of a set of nucleic acid fragments). In the shuffling procedures herein, these cleavage fragments can be used in conjunction with family gene shuffling oligonucleotides, e.g., in one or more recombination reaction.

Recursive methods of oligonucleotide shuffling are provided. As noted herein, recombinant nucleic acids generated synthetically using oligonucleotides can be cleaved and shuffled by standard nucleic acid shuffling methodologies, or the nucleic acids can be sequenced and used to design a second set of family shuffling oligonucleotides which are used to recombine the recombinant nucleic acids. Either, or both, of these recursive techniques can be used for subsequent rounds of recombination and can also be used in conjunction with rounds of selection of recombinant products. Selection steps can follow one or several rounds of recombination, depending on the desired diversity of the recombinant nucleic acids (the more rounds of recombination which are performed, the more diverse the resulting population of recombinant nucleic acids).

The use of family gene shuffling oligonucleotides in recombination reactions herein provides for domain switching of domains of sequence identity or diversity between homologous nucleic acids, e.g., where recombinants resulting from the recombination reaction provide recombinant nucleic acids with a sequence domain from a first nucleic acid embedded within a sequence corresponding to a second nucleic acid, e.g., where the region most similar to the embedded region from the second nucleic acid is not present in the recombinant nucleic acid.

One particular advantage of the present invention is the ability to recombine homologous nucleic acids with low sequence similarity, or even to recombine non-homologous nucleic acids. In these methods, one or more set of fragmented nucleic acids are recombined with a with a set of crossover family diversity oligonucleotides. Each of these crossover oligonucleotides have a plurality of sequence diversity domains corresponding to a plurality of sequence diversity domains from homologous or non-homologous nucleic acids with low sequence similarity. The fragmented oligonucleotides, which are derived from one or more homologous or non-homologous nucleic acids can hybridize to one or more region of the crossover oligos, facilitating recombination.

Methods of family shuffling PCR amplicons using family diversity oligonucleotide primers are also provided. In these methods, a plurality of non-homogeneous homologous template nucleic acids are provided. A plurality of PCR primers which hybridize to a plurality of the plurality of non-homogeneous homologous template nucleic acids are also provided. A plurality of PCR amplicons are produced by PCR amplification of the plurality of template nucleic acids with the plurality of PCR primers, which are then recombined. Typically, sequences for the PCR primers are selected by aligning sequences for the plurality of non-homogeneous homologous template nucleic acids and selecting PCR primers which correspond to regions of sequence similarity.

A variety of compositions for practicing the above methods and which result from practicing the above methods are also provided. Compositions which include a library of oligonucleotides having a plurality of oligonucleotide member types are one example. The oligonucleotide member types corresponding to a plurality of subsequence regions of a plurality of members of a selected set of a plurality of homologous target sequences. The plurality of subsequence regions can include, e.g., a plurality of overlapping or non-overlapping sequence regions of the selected set of homologous target sequences. The oligonucleotide member types typically each have a sequence identical to at least one subsequence from at least one of the selected set of homologous target sequences. Any of the oligonucleotide types and sets described above, or elsewhere herein, can be included in the compositions of the invention (e.g., family shuffling oligonucleotides, crossover oligonucleotides, domain switching oligonucleotides, etc.). The oligonucleotide member types can include a plurality of homologous oligonucleotides corresponding to a homologous region from the plurality of homologous target sequences. In this embodiment, each of the plurality of homologous oligonucleotides have at least one variant subsequence. Libraries of nucleic acids and encoded proteins which result from practicing oligonucleotide-mediated recombination as noted herein are also a feature of the invention.

Compositions optionally include components which facilitate recombination reactions, e.g., a polymerase, such as a thermostable DNA polymerase (e.g., taq, vent or any of the many other commercially available polymerases) a recombinase, a nucleic acid synthesis reagent, buffers, salts, magnesium, one or more nucleic acid having one or more of the plurality of members of the selected set of homologous target sequences, and the like.

Kits comprising the compositions of the invention, e.g., in containers, or other packaging materials, e.g., with instructional materials for practicing the methods of the invention are also provided. Uses for the compositions and kits herein for practicing the methods are also provided.

Definitions

Unless otherwise indicated, the following definitions supplement those in the art.

Nucleic acids are "homologous" when they are derived, naturally or artificially, from a common ancestor sequence. During natural evolution, this occurs when two or more descendent sequences diverge from a parent sequence over time, i.e., due to mutation and natural selection. Under artificial conditions, divergence occurs, e.g., in one of two basic ways. First, a given sequence can be artificially recombined with another sequence, as occurs, e.g., during typical cloning, to produce a descendent nucleic acid, or a given sequence can be chemically modified, or otherwise manipulated to modify the resulting molecule. Alternatively, a nucleic acid can be synthesized de novo, by synthesizing a nucleic acid which varies in sequence from a selected parental nucleic acid sequence. When there is no explicit knowledge about the ancestry of two nucleic acids, homology is typically inferred by sequence comparison between two sequences. Where two nucleic acid sequences show sequence similarity over a significant portion of each of the nucleic acids, it is inferred that the two nucleic acids share a common ancestor. The precise level of sequence similarity which establishes homology varies in the art depending on a variety of factors.

For purposes of this disclosure, two nucleic acids are considered homologous where they share sufficient sequence identity to allow direct recombination to occur between the two nucleic acid molecules. Typically, nucleic acids utilize regions of close similarity spaced roughly the same distance apart to permit recombination to occur. The recombination can be in vitro or in vivo.

It should be appreciated, however, that one advantage of certain features of the invention is the ability to recombine more distantly related nucleic acids than standard recombination techniques permit. In particular, sequences from two nucleic acids which are distantly related, or even not detectably related can be recombined using cross-over oligonucleotides which have subsequences from two or more different non-homologous target nucleic acids, or two or more distantly related nucleic acids. However, where the two nucleic acids can only be indirectly recombined using oligonucleotide intermediates as set forth herein, they are considered to be "non-homologous" for purposes of this disclosure.

A "set" as used herein refers to a collection of at least two molecules types, and typically includes at least about, e.g., 5, 10, 50, 100, 500, 1,000 or more members, depending on the precise intended use of the set.

A set of "family gene shuffling oligonucleotides" is a set of synthesized oligonucleotides derived from a selected set of homologous nucleic acids. The oligonucleotides are derived from a selected set of homologous nucleic acids when they (individually or collectively) have regions of sequence identity (and, optionally, regions of sequence diversity) with more than one of the homologous nucleic acids. Collectively, the oligonucleotides typically correspond to a substantial portion of the full length of the homologous nucleic acids of the set of homologous nucleic acids, e.g., the oligonucleotides correspond over a substantial portion of the length of the homologous nucleic acids (e.g., the oligonucleotides of the set collectively correspond to e.g., 25% or more, often 35% or more, generally 50% or more, typically 60% or more, more typically 70% or more, and in some applications, 80%, 90% or 100% of the full-length of each of the homologous nucleic acids). Most commonly, the family gene shuffling oligonucleotides include multiple member types, each having regions of sequence identity to at least one member of the selected set of homologous nucleic acids (e.g., about 2, 3, 5, or 10 or more member types).

A "cross-over" oligonucleotide has regions of sequence identity to at least two different members of a selected set of nucleic acids, which are optionally homologous or non-homologous.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biolog—Hybridization with Nucleic Acid Probes* part I chapter 2 "Overview of principles of hybridization and the strategy of nucleic acid probe assays," Elsevier, N.Y., as well as in Ausubel, supra.

Two nucleic acids "correspond" when they have the same or complementary sequences, or when one nucleic acid is a subsequence of the other, or when one sequence is derived, by natural or artificial manipulation, from the other.

Nucleic acids are "elongated" when additional nucleotides (or other analogous molecules) are incorporated into the nucleic acid. Most commonly, this is performed with a polymerase (e.g., a DNA polymerase), e.g., a polymerase which adds sequences at the 3' terminus of the nucleic acid.

Two nucleic acids are "recombined" when sequences from each of the two nucleic acids are combined in a progeny nucleic acid. Two sequences are "directly" recombined when both of the nucleic acids are substrates for recombination. Two sequences are "indirectly recombined" when the sequences are recombined using an intermediate such as a cross-over oligonucleotide. For indirect recombination, no more than one of the sequences is an actual substrate for recombination, and in some Lases, neither sequence is a substrate for recombination (i.e., when one or more oligonucleotide(s) corresponding to the nucleic acids are hybridized and elongated).

A collection of "fragmented nucleic acids" is a collection of nucleic acids derived by cleaving one or more parental nucleic acids (e.g., with a nuclease, or via chemical cleavage), or by producing subsequences of the parental sequences in any other manner, such as partial chain elongation of a complementary nucleic acid.

A "full-length protein" is a protein having substantially the same sequence domains as a corresponding protein encoded by a natural gene. The protein can have modified sequences relative to the corresponding naturally encoded gene (e.g., due to recombination and selection), but is at least 95% as long as the naturally encoded gene.

A "DNase enzyme" is an enzyme which catalyzes cleavage of a DNA, in vitro or in vivo. A wide variety of DNase enzymes are well known and described, e.g., in Sambrook, Berger and Ausubel (all supra) and many are commercially available.

A "nucleic acid domain" is a nucleic acid region or subsequence. The domain can be conserved or not conserved between a plurality of homologous nucleic acids. Typically a domain is delineated by comparison between two or more sequences, i.e., a region of sequence diversity between sequences is a "sequence diversity domain," while a region of similarity is a "sequence similarity domain." Domain switching" refers to the ability to switch one nucleic acid region from one nucleic acid with a second domain from a second nucleic acid.

A region of "high sequence similarity" refers to a region that is 90% or more identical to a second selected region when aligned for maximal correspondence (e.g., manually or using the common program BLAST set to default parameters). A region of "low sequence similarity" is 60% or less identical, more preferably, 40% or less identical to a second selected region, when aligned for maximal correspondence (e.g., manually or using BLAST set with default parameters).

A "PCR amplicon" is a nucleic acid made using the polymerase chain reaction (PCR). Typically, the nucleic acid is a copy of a selected nucleic acid. A "PCR primer" is a nucleic acid which hybridizes to a template nucleic acid and permits chain elongation using a thermostable polymerase under appropriate reaction conditions.

A "library of oligonucleotides" is a set of oligonucleotides. The set can be pooled, or can be individually accessible. Oligonucleotides can be DNA, RNA or combinations of RNA and DNA (e.g., chimeraplasts).

DETAILED DISCUSSION OF THE INVENTION

Figure 1:
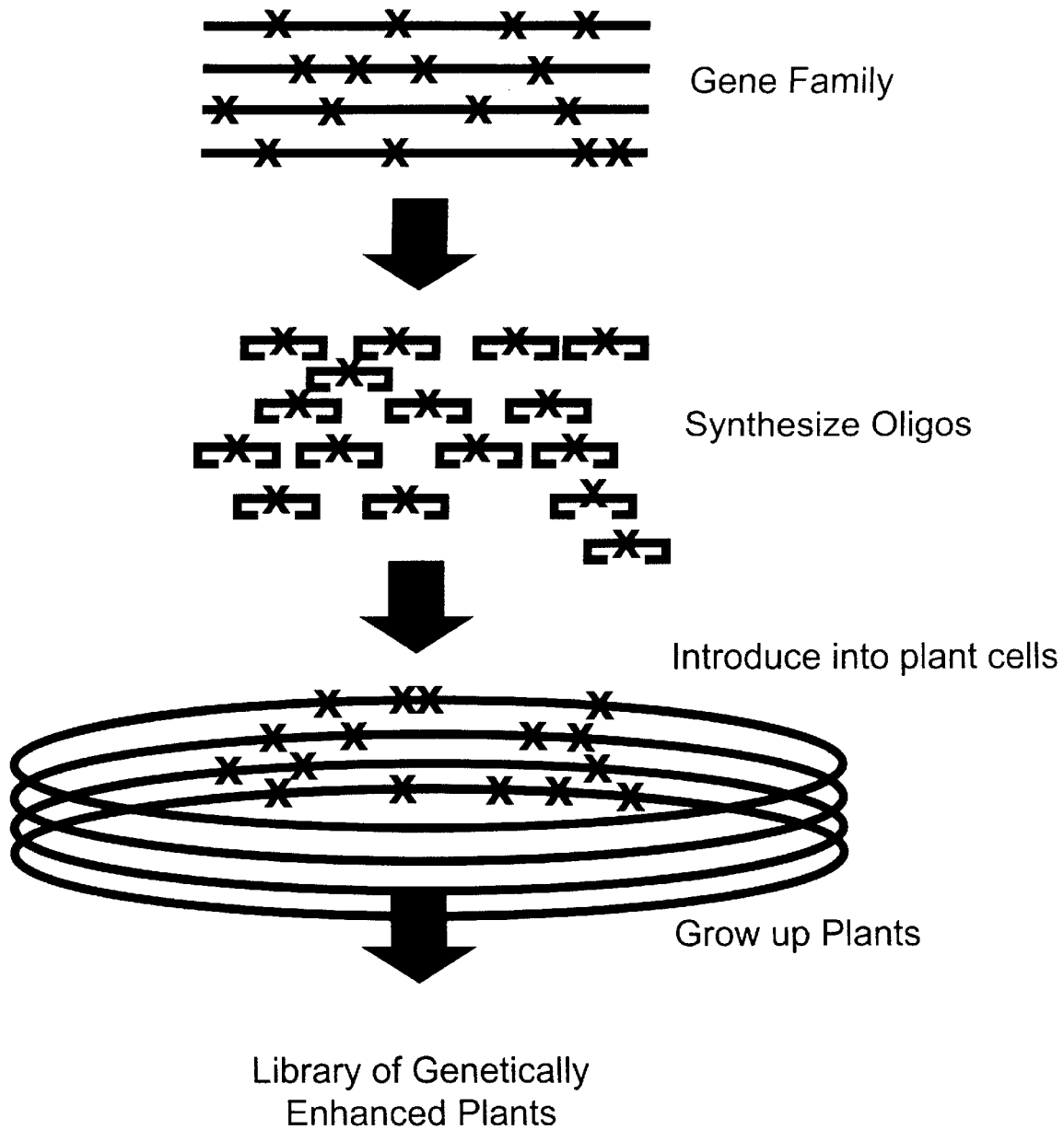
FIG. 1 is a schematic showing oligonucleotide-directed in vivo shuffling using chimeraplasts.

The present invention relates to improved formats for nucleic acid shuffling. In particular, by using selected oligonucleotide sets as substrates for recombination and/or gene synthesis, it is possible to dramatically speed the shuffling process. Moreover, it is possible to use oligonucleotide intermediates to indirectly recombine nucleic acids which could not otherwise be recombined. Direct access to sequences to be combined is not necessary, as the sequences can be recombined indirectly through oligonucleotide intermediates.

In brief, a family of homologous nucleic acid sequences are first aligned, e.g. using available computer software to select regions of identity/similarity and regions of diversity. A plurality (e.g., 2, 5, 10, 20, 50, 75, or 100 or more) of oligonucleotides corresponding to at least one region of diversity (and ordinarily at least one region of similarity) are synthesized. These oligonucleotides can be shuffled directly, or can be recombined with one or more of the family of nucleic acids.

This oligonucleotide-based recombination of related nucleic acids can be combined with a number of available standard shuffling methods. For example, there are several procedures now available for shuffling homologous nucleic acids, such as by digesting the nucleic acids with a DNase, permitting recombination to occur and then regenerating full-length templates, i.e., as described in Stemmer (1998) DNA MUTAGENESIS BY RANDOM FRAGMENTATION AND REASSEMBLY U.S. Patent 5,830,721). Thus, in one embodiment of the invention, a full-length nucleic acid which is identical to. or homologous with, at least one of the homologous nucleic acids is provided, cleaved with a DNase, and the resulting set of nucleic acid fragments are recombined with the plurality of family gene shuffling oligonucleotides. This combination of methods can be advantageous, because the DNase-cleavage fragments form a "scaffold" which can be reconstituted into a full length sequence—an advantage in the event that one or more synthesized oligo in the synthesized set is defective.

However, one advantage of the present invention is the ability to recombine several regions of diversity among homologous nucleic acids, even without the homologous nucleic acids, or cleaved fragments thereof, being present in the recombination mixture. Resulting shuffled nucleic acids can include regions of diversity from different nucleic acids, providing for the ability to combine different diversity domains in a single nucleic acid. This provides a very powerful method of accessing natural sequence diversity.

In general, the methods herein provide for "oligonucleotide mediated shuffling" in which oligonucleotides corresponding to a family of related homologous nucleic acids which are recombined to produce selectable nucleic acids. The technique can be used to recombine homologous or even non-homologous nucleic acid sequences. When recombining homologous nucleic acids, sets of overlapping family gene shuffling oligonucleotides (which are derived, e.g., by comparison of homologous nucleic acids and synthesis of oligonucleotide fragments) are hybridized and elongated (e.g., by reassembly PCR), providing a population of recombined nucleic acids, which can be selected for a desired trait or property. Typically, the set of overlapping family shuffling gene oligonucleotides include a plurality of oligonucleotide member types which have consensus region subsequences derived from a plurality of homologous target nucleic acids.

Typically, family gene shuffling oligonucleotide are provided by aligning homologous nucleic acid sequences to select conserved regions of sequence identity and regions of sequence diversity. A plurality of family gene shuffling oligonucleotides are synthesized (serially or in parallel) which correspond to at least one region of sequence diversity.

Sets of fragments, or subsets of fragments used in oligonucleotide shuffling approaches can be partially provided by cleaving one or more homologous nucleic acids (e.g., with a DNase), as well as by synthesizing a set of oligonucleotides corresponding to a plurality of regions of at least one nucleic acid (typically oligonucleotides corresponding to a partial or full-length nucleic acid are provided as members of the set of nucleic acid "fragments," a term which encompasses both cleavage fragments and synthesized oligonucleotides). In the shuffling procedures herein, these cleavage fragments can be used in conjunction with family gene shuffling oligonucleotides, e.g., in one or more recombination reaction to produce recombinant nucleic acids.

The following provides details and examples regarding sequence alignment, oligonucleotide construction and library generation, shuffling procedures and other aspects of the present invention.

ALIGNING HOMOLOGOUS NUCLEIC ACID SEQUENCES TO SELECT CONSERVED REGIONS OF SEQUENCE IDENTITY AND REGIONS OF SEQUENCE DIVERSITY

In one aspect, the invention provides for alignment of nucleic acid sequences to determine regions of sequence identity or similarity and regions of diversity. The set of overlapping family shuffling gene oligonucleotides can comprise a plurality of oligonucleotide member types which comprise consensus region subsequences derived from a plurality of homologous target nucleic acids. These consensus region subsequences are determined by aligning homologous nucleic acids and identifying regions of identity or similarity.

In one embodiment, homologous nucleic acid sequences are aligned, and at least one conserved region of sequence identity and a plurality of regions of sequence diversity are selected. The plurality of regions of sequence diversity provide a plurality of domains of sequence diversity. Typically, a plurality of family gene shuffling oligonucleotides corresponding to the plurality of domains of sequence diversity are synthesized and used in the various recombination protocols noted herein or which are otherwise available.

Alignment of Homologous Nucleic Acids

Typically, the invention comprises first aligning identical nucleic acids, or regions of nucleic acid similarity, e.g., for sequences available from any of the publicly available or proprietary nucleic acid databases. Public database/search services include Genbank®, Entrez®, EMBL, DDBJ and those provided by the NCBI. Many additional sequence databases are available on the internet or on a contract basis from a variety of companies specializing in genomic information generation and/or storage.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides refers to two or more sequences or subsequences that have at least about 50%, preferably 80%, most preferably 90–95% nucleotide or amino acid residue identity, when compared and aligned for maximum correspondence, as measured using one of the following sequence comparison algorithms or by visual inspection. Such "substantially identical" sequences are typically considered to be homologous.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math*. 2:482 (1981), by the homology alignment algorithm of Needleman & Wunsch, *J. Mol. Biol*. 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr. Madison, Wis.), or by visual inspection (see generally, Ausubel et al., infra).

One example algorithm that is suitable for determining percent sequence identity and sequence similarity is the BLAST algorithm, which is described in Altschul et al., *J. Mol. Biol*. 215:403–410 (1990). Software for performing BLAST analyses is publicly available through the National Center for Biotechnology Information (http://www.ncbi.nlm.nih.gov/). This algorithm involves first identifying high scoring sequence pairs (HSPS) by identifying short words of length W in the query sequence, which either match or satisfy some positive-valued threshold score T when aligned with a word of the same length in a database sequence. T is referred to as the neighborhood word score threshold (Altschul et al. supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (and, therefore, likely homologous) if the smallest sum probability in a comparison of the test nucleic acid to the reference nucleic acid is less than about 0.1, more preferably less than about 0.01, and most preferably less than about 0.001.

Oligonucleotide Synthesis

In one aspect, the invention comprises synthesizing a plurality of family gene shuffling oligonucleotides, e.g., corresponding to at least one region of sequence diversity. Typically sets of family gene shuffling oligonucleotides are produced, e.g., by sequential or parallel oligonucleotide synthesis protocols.

Oligonucleotides, e.g., whether for use in in vitro amplification/gene reconstruction/reassembly methods, or to provide sets of family gene shuffling oligonucleotides, are typically synthesized chemically according to the solid phase phosphoramidite triester method described by Beaucage and Caruthers (1981), *Tetrahedron Letts*., 22(20): 1859–1862, e.g., using an automated synthesizer, as described in Needham-VanDevanter et al. (1984) *Nucleic Acids Res*., 12:6159–6168. A wide variety of equipment is commercially available for automated oligonucleotide synthesis. Multi-nucleotide synthesis approaches (e.g., tri-nucleotide synthesis), as discussed, supra, are also useful.

Moreover, essentially any nucleic acid can be custom ordered from any of a variety of commercial sources, such as The Midland Certified Reagent Company (mcrc@oligos.com), The Great American Gene Company (http://www.genco.com), ExpressGen Inc. (www.expressgen.com), Operon Technologies Inc. (Alameda, Calif.) and many others.

Synthetic Library Assembly

Libraries of family gene shuffling oligonucleotides are provided. For example, homologous genes of interest are aligned using a sequence alignment program such as BLAST, as described above. Nucleotides corresponding to amino acid variations between the homologs are noted. Oligos for synthetic gene shuffling are designed which comprise one (or more) nucleotide difference to any of the aligned homologous sequences, i.e., oligos are designed that are identical to a first nucleic acid, but which incorporate a residue at a position which corresponds to a residue of a nucleic acids homologous, but not identical to the first nucleic acid.

Preferably, all of the oligonucleotides of a selected length (e.g., about 20, 30, 40, 50, 60, 70, 80, 90, or 100 or more nucleotides) which incorporate all possible nucleic acid variants are made. This includes X oligonucleotides per X sequence variations, where X is the number of different sequences at a locus. The X oligonucleotides are largely identical in sequence, except for the nucleotide(s) representing the variant nucleotide(s). Because of this similarity, it can be advantageous to utilize parallel or pooled synthesis strategies in which a single synthesis reaction or set of reagents is used to make common portions of each oligonucleotide. This can be performed e.g., by well-known solid-phase nucleic acid synthesis techniques, or, e.g., utilizing array-based oligonucleotide synthetic methods (see e.g., Fodor et al. (1991) *Science*, 251: 767–777; Fodor (1997) "Genes, Chips and the Human Genome" FASEB Journal. 11:121–121; Fodor (1997) "Massively Parallel Genomics" *Science*. 277:393–395; and Chee et al. (1996) "Accessing Genetic Information with High-Density DNA Arrays" Science 274:610–614).

In one aspect, oligonucleotides are chosen so that only encoded amino acid alterations are considered in the synthesis strategy. In this strategy, after aligning a family of homologous nucleic acids, family shuffling oligos are synthesized to be degenerate only at those positions where a base change results in an alteration in an encoded polypeptide sequence. This has the advantage of requiring fewer degenerate oligonucleotides to achieve the same degree of diversity in encoded products, thereby simplifying the synthesis of the set of family gene shuffling oligonucleotides.

In synthesis strategies in general, the oligonucleotides have at least about 10 bases of sequence identity to either side of a region of variance to ensure reasonably efficient recombination. However, flanking regions with identical bases can have fewer identical bases (e.g., 5, 6, 7, 8, or 9) and can, of course, have larger regions of identity (e.g., 11, 12, 13, 14, 15, 16, 17, 18, ,19, 20, 25, 30, 50, or more).

During gene assembly, oligonucleotides can be incubated together and reassembled using any of a variety of polymerase-mediated reassembly methods, e.g., as described herein and as known to one of skill. Selected oligonucleotides can be "spiked" in the recombination mixture at any selected concentration, thus causing preferential incorporation of desirable modifications.

For example, during oligonucleotide elongation, hybridized oligonucleotides are incubated in the presence of a nucleic acid polymerase, e.g., Taq, Klenow, or the like, and dNTP's (i.e., dATP, dCTP, dGTP and dTTP). If regions of sequence identity are large, Taq or other high-temperature polymerase can be used with a hybridization temperature of between about room temperature and, e.g., about 65° C. If the areas of identity are small, Klenow, Taq or polymerases can be used with a hybridization temperature of below room temperature. The polymerase can be added to nucleic acid fragments (oligonucleotides plus any additional nucleic acids which form a recombination mixture) prior to, simultaneously with, or after hybridization of the oligonucleotides and other recombinationcomponents. As noted elsewhere in this disclosure, certain embodiments of the invention can involve denaturing the resulting elongated double-stranded nucleic acid sequences and then hybridizing and elongating those sequences again. This cycle can be repeated for any desired number of times. The cycle is repeated e.g., from about 2 to about 100 times.

Library Spiking

The family oligonucleotides can also be used to vary the nucleic acids present in a typical shuffling mixture; e.g., a mixture to DNase fragments of one or more gene(s) from a homologous set of genes. In one aspect, all of the nucleic acid to be shuffled are aligned as described above. Amino acid variations are noted and/or marked (e.g., in an integrated system comprising a computer running appropriate sequence alignment software, or manually, e.g., on a printout of the sequences or sequence alignments). As above, family shuffling oligos are designed to incorporate some or all of the amino acid variations coded by the natural sequence diversity for the aligned nucleic acids. One or more nucleic acids corresponding to the homologous set of aligned nucleic acids are cleaved (e.g., using a DNase, or by chemical cleavage). Family shuffling oligos are spiked into the mixture of cleaved nucleic acids, which are then recombined and reassembled into full-length sequences using standard techniques.

To determine the extent of oligonucleotide incorporation any approach which distinguishes similar nucleic acids can be used. For example, the reassembled nucleic acids can be cloned and sequenced, or amplified (in vitro or by cloning, e.g., into a standard cloning vector) and cleaved with a restriction enzyme which specifically recognizes a particular polymorphic sequence present in the family shuffling oligos, but not present in the same position in the original cleaved nucleic acid(s).

In another embodiment, oligonucleotides are selected which incorporate one or more sequence variation corresponding to an amino acid polymorphism, but which eliminate polymorphic nucleotide variations between nucleic acid sequences which correspond to silent substitutions. One advantage of this strategy is that the elimination of silent substitutions can make a given sequence more similar to a given substrate for recombination (e.g., a selected target nucleic acid). This increased similarity permits nucleic acid recombination among sequences which might otherwise be too diverse for efficient recombination.

For example, a selected nucleic amid can be PCR amplified using standard methods. The selected nucleic acid is cleaved and mixed with a library of family gene shuffling oligonucleotides which are rendered as similar as possible to the corresponding sequences of the selected nucleic acid by making the oligonucleotides include the same silent substitution set found in the selected nucleic acid. The oligonucleotides are spiked at a selected concentration into the cleavage mixture, which is then reassembled into full-length sequences. The quality of the resulting library (e.g., frequency at which the oligos are incorporated into the reassembled sequences) is checked, as noted above, by cloning (or otherwise amplifying) and sequencing and/or restriction digesting the reassembled sequences.

PCR elongation strategies can also be used to make libraries using different molar ratios of oligonucleotides in the recombination mixtures (see also, e.g., WO 97/20078, WO 98/42832 and WO 98/01581).

Iterative Oligonucleotide Formats

In one aspect, the present invention provides iterative oligonucleotide-mediated recombination formats. These formats can be combined with standard recombination methods, also, optionally, in an iterative format.

In particular, recombinant nucleic acids produced by oligonucleotide-mediated recombination can be screened for activity and sequenced. The sequenced recombinant nucleic acids are aligned and regions of identity and diversity are identified. Family shuffling oligonucleotides are then selected for recombination of the sequenced recombinant nucleic acids. This process of screening, sequencing active recombinant nucleic acids and recombining the active recombinant nucleic acids can be iteratively repeated until a molecule with a desired property is obtained.

In addition, recombinant nucleic acids made using family shuffling oligonucleotides can be cleaved and shuffled using standard recombination methods, which are, optionally, reiterative. Standard recombination can be used in conjunction with oligonucleotide shuffling and either or both steps are optionally reiteratively repeated.

One useful example of iterative shuffling by oligonucleotide mediated recombination of family oligonucleotides occurs when extremely fine grain shuffling is desired.

For example, small genes encoding small protein such as defensins (antifungal proteins of about 50 amino acids) EF40 (an antifungal protein family of about 28 amino acids), peptide antibiotics, peptide insecticidal proteins, peptide hormones, many cytokines and many other small proteins, are difficult to recombine by standard recombination methods, because the recombination often occurs with a frequency that is roughly the same as the size of the gene to be recombined, limiting the diversity resulting from recombination. In contrast, oligonucleotide-mediated recombination methods can recombine essentially any region of diversity in any set of sequences, with recombination events (e.g., crossovers) occurring at any selected base-pair.

Thus, libraries of sequences prepared by recursive oligonucleotide mediated recombination are optionally screened and selected for a desired property, and improved (or otherwise desirable) clones are sequenced with the process being iteratively repeated to generate additional libraries of nucleic acids. Thus, additional recombination rounds are performed either by standard fragmentation-based recombination methods, or by sequencing positive clones, designing appropriate family shuffling oligonucleotides and performing a second round of recombination/selection to produce an additional library (which can be recombined as described). In addition, libraries made from different recombination rounds can also be recombined, either by sequencing/oligonucleotide recombination or by standard recombination methods.

Crossover PCR Shuffling

In one aspect, the present invention provides for shuffling of distantly related or even non-homologous sequences. In this embodiment, PCR crossover oligonucleotides are designed with a first region derived from a first nucleic acid and a second region corresponding to a second nucleic acid. Additional oligos are designed which correspond to either the first or second nucleic acid, and which hake sequences that are complementary (or identical) to the crossover oligos. By recombining these oligos (i.e., hybridizing them and then elongating the hybridized oligonucleotides in successive polymerase-mediated elongation reactions), a substrate is provided which can recombine with either the first or second nucleic acid, and which will, at the same time, incorporate sequences from the other nucleic acid.

IN VIVO OLIGONUCLEOTIDE RECOMBINATION UTILIZING FAMILY SHUFFLING CHIMERAPLASTS

Chimeraplasts are synthetic RNA-DNA hybrid molecules which have been used for "genetic surgery" in which one or a few bases in a genomic DNA are changed by recombination with the chimeric molecule. The chimeraplasts are chimeric nucleic acids composed of contiguous stretches of RNA and DNA residues in a duplex conformation with double hairpin caps on the ends of the molecules (Yoon et al. (1996) *PNAS* 93:2071–2076). The RNA-DNA sequence is designed to align with the sequence of a locus to be altered by recombination with the chimeraplast, with the chimeraplast having the desired change in base sequence for the locus. The host cell repair machinery converts the host cell sequence to that of the chimeraplast. For brief reviews of the technique see, Bartlett (1998) *Nature Biotechnology* 16:1312; Strauss (1998) *Nature Medicine* 4:274–275.

This strategy has been used for targeted correction of a point mutation in the gene for human liver/kidney/bone alkaline phosphatase encoded on an episomal DNA in mammalian cells (Yoon, id.). The strategy was also used for correction of the mutation responsible for sickle cell anemia in genomic DNA in lymphoblastoid cells (Cole-Strauss et al. (1996) *Science* 1386–1389). Alexeev and Yoon (1998) *Nature Biotechnology* 1343–1346 describe the use of a hybrid RNA-DNA oligonucleotide (an "RDO") to make a point correction in the mouse tyrosinase gene, resulting in correction of an albino mutation in mouse cells and production of black pigmentation by the cells. Kren et al. (1998) *Nature Medicine* 4(3):285–290 describe in vivo site-directed mutagenesis of the factor IX gene by chimeric RNA/DNA oligonucleotides. Xiang et al (1997) *J. Mol. Med.* 75:829–835 describe targeted gene conversion in a mammalian CD34[+]-enriched cell population using a chimeric RNA-DNA oligonucleotide. Kren et al. (1997) *Herpatology* 25(6):1462–1468 describe targeted nucleotide exchange in the alkaline phosphatase gene of Hu-H-7 cells mediated by a chimeric RNA-DNA oligonucleotide.

In one aspect of the present invention, the family shuffling oligonucleotides are chimeraplasts. In this embodiment, family shuffling oligonucleotides are made as set forth herein, to additionally include structural chimeraplast features. For example, in the references noted above, DNA-RNA oligos are synthesized according to standard phosphoramidite coupling chemistries (the nucleotides utilized optionally include non-standard nucleotides such as 2O methylated RNA nucleotides). The oligos have a "dual hairpin" structure (e.g., having a T loop at the ends of the structure) as set forth in the references noted above.

The set of family shuffling chimeraplasts each include regions of identity to a target gene of interest, and regions of diversity corresponding to the diversity (i.e., the sequence variation for a particular subsequence) found in the target gene of interest. As set forth in FIG. 1, the set of oligonucleotides is transduced into cells (e.g., plant cells), where the chimeraplasts recombine with a sequence of interest in the genome of the cells, thereby creating a library of cells with at least one region of diversity at a target gene of interest. The library is then screened and selected as described herein. Optionally, the selected library members are subjected to an additional round of chimeraplast recombination with the same or different set of chimeraplast oligonucleotides, followed by selection/screening assays as described.

For example, chimeraplasts are synthesized with sequences which correspond to regions of sequence diversity observed following an alignment of homolgous nucleic acids. That is, the chimeraplasts each contain one or a few nucleotides which, following incorporation of the chimeraplasts into one or more target sequences, results in conversion of a subsequence of a gene into a subsequence found in an homologous gene. By transducing a library of homologous chimeraplast sequences into a population of cells, the target gene of interest within the cells is converted at one or more positions to a sequence derived from one or more homologous sequences. Thus, the effect of transducing the cell population with the chimeraplast library is to create a library of target genes corresponding to the sequence diversity found in genes homologous to the target sequence.

Chimeraplasts can also be similarly used to convert the target gene at selected positions with non-homologous sequence choices, e.g., where structural or other information suggests the desirability of such a conversion. In this embodiment, the chimeraplasts include sequences corresponding to non-homologous sequence substitutions.

Optionally, the chimeraplasts, or a co-transfected DNA, can incorporate sequence tags, selectable markers, or other structural features to permit selection or recovery of cells in which the target gene has recombined with the chimeraplast. For example, a co-transfected DNA can include a marker such as drug resistance, or expression of a detectable marker (e.g., Lac Z, or green fluorescent protein).

In addition, sequences in the chimeraplast can be used as purification or amplification tags. For example, a portion of the chimeraplast can be complementary to a PCR primer. In this embodiment, PCR primers are used to synthesize recombinant genes from the cells of the library. Similarly, PCR primers can bracket regions of interest, including regions in which recombination between a chimeraplast and a standard DNA occurs. Other PCR, restriction enzyme digestion and/or cloning strategies which result in the isolation of nucleic acids resulting from recombination between the chimeraplast can also be used to recover the recombined nucleic acid, which is optionally recombined with additional nucleic acids. Reiterative cycles of chimeraplast-mediated recombination, recovery of recombinant nucleic acids and recombination of the recovered nucleic acids can be performed using standard recombination methods. Selection cycles can be performed after any recombination event to select for desirable nucleic acids, or, alternatively, several rounds of recombination can be performed prior to performing a selection step.

LIBRARIES OF CHIMERAPLASTS AND OTHER GENE RECOMBINATION VEHICLES

As noted above, chimeraplasts are generally useful structures for modification of nucleotide sequences in target genes, in vivo. Accordingly, structures which optimize chimeraplast activity are desirable. Thus, in addition to the use of chimeraplasts in in vitro and in vivo recombination formats as noted, the present invention also provides for the optimization of chimeraplast activity in vitro and in vivo, as well as for a number of related libraries and other compositions.

In particular, a marker can be incorporated into a library of related chimeraplasts. The marker is placed between the ends of the chimeraplast in the region of the molecule which is incorporated into a target nucleic acid following recombination between the chimeraplast and the target nucleic acid. For example, the marker can cause a detectable phenotypic effect in a cell in which recombination occurs, or the marker can simply lead to a change in the target sequence which can be detected by standard nucleic acid sequence detection techniques (e.g., PCR amplification of the sequence or of a flanking sequence, LCR, restriction enzyme digestion of a sequence created by a recombination event, binding of the recombined nucleic acid to an array, and/or sequencing of the recombined nucleic acid, etc.). Ordinarily, the regions of sequence difference are determined to provide an indication of which sequences have increased recombination rates.

The library of related chimeraplasts includes chimeraplasts with regions of sequence divergence in the T loop hairpin regions and in the region between the T loop hairpin region flanking the marker. This divergence can be produced by synthetic strategies which provide for production of heterologous sequences as described herein.

For example, synthetic strategies utilizing chimeraplasts which are largely identical in sequence, except for the nucleotide(s) representing the variant nucleotide(s) are produced to simplify synthetic strategies. Because of this similarity, parallel or pooled synthesis strategies can be used in which a single synthesis reaction or set of reagents is used to make common portions of each oligonucleotide. This can be performed e.g., by well-known solid phase nucleic acid synthesis techniques, e.g., in a commercially available oligonucleotide synthesizer, or, e.g., by utilizing array-based oligonucleotide synthetic methods (see e.g., Fodor et al. (1991) Science, 251: 767–777; Fodor (1997) "Genes, Chips and the Human Genome" FASEB Journal. 11: 121–121; Fodor (1997) "Massively Parallel Genomics" Science. 277:393–395; and Chee et al. (1996) "Accessing Genetic Information with High-Density DNA Arrays" Science 274:610–614). Accordingly, one feature of the present invention is a library of chimeraplasts produced by these methods, i.e., a library of chimeraplasts which share common sequence elements, including e.g., a common marker, as well as regions of difference, e.g., different sequences in the hairpin regions of the molecule.

The library which is produced by these methods is screened for increased recombination rates as noted above. Library members which are identified as having increased rates of recombination are optionally themselves recombined to produce libraries of recombined chimeraplasts. Recombination is ordinarily performed by assessing the sequences of the members which initially display increased recombination rates, followed by synthesis of chimeraplasts which display structural similarity to at least two of these members. This process can be iteratively repeated to create new "recombinant" chimeraplasts with increased recombination activity, as well as libraries of such chimeraplasts.

Other recombination molecules can similarly be produced by these methods. For example, Cre-Lox sites, Chi sites and other recombination facilitating sequences in cell transduction/transformation vectors are varied and selected in the same manner as noted above. Where the sequences are simple DNA sequences, they can be recombined either by the synthetic methods noted herein, and/or by standard DNA shuffling methods.

CODON-VARIED OLIGONUCLEOTIDES

Codon-varied oligonucleotides are oligonucleotides, similar in sequence but with one or more base variations, where-the variations correspond to at least one encoded amino acid difference. They can be synthesized utilizing tri-nucleotide, i.e., codon-based phosphoramidite coupling chemistry, in which tri-nucleotide phosphoramidites representing codons for all 20 amino acids are used to introduce entire codons into oligonucleotide sequences synthesized by this solid-phase technique. Preferably, all of the oligonucleotides of a selected length (e.g., about 20, 30, 40, 50, 60, 70, 80, 90, or 100 or more nucleotides) which incorporate the chosen nucleic acid sequences are synthesized. In the present invention, codon-varied oligonucleotide sequences can be based upon sequences from a selected set of homologous nucleic acids.

The synthesis of tri-nucleotide phoshoramidites, their subsequent use in oligonucleotide synthesis, and related issues are described in, e.g., Virnekäs, B., et al., (1994) Nucleic Acids Res., 22, 5600–5607, Kayushin, A. L. et al., (1996) Nucleic Acids Res., 24, 3748–3755, Huse, U.S. Pat. No. 5,264,563 "PROCESS FOR SYNTHESIZING OLIGONUCLEOTIDES WITH RANDOM CODONS", Lyttle et al., U.S. Pat. No. 5,717,085 "PROCESS FOR PREPARING CODON AMIDITES", Shortle et al., U.S. Pat. No. 5,869,644 "SYNTHESIS OF DIVERSE AND USEFUL COLLECTIONS OF OLIGONUCLEOTIDES"; Greyson, U.S. Pat. No. 5,789,577 "METHOD FOR THE CONTROLLED SYNTHESIS OF POLYNUCLEOTIDE MIXTURES WHICH ENCODE DESIRED MIXTURES OF PEPTIDES"; and Huse, WO 92/06176 "SURFACE EXPRESSION LIBRARIES OF RANDOMIZED PEPTIDES".

Codon-varied oligonucleotides can be synthesized using various trinucleotide related techniques, e.g., the trinucleotide synthesis format and the split-pool synthesis format. The chemistry involved in both the trinucleotide and the split-pool codon-varied oligonucleotide synthetic methods is well known to those of skill. In general, both methods utilize phosphoramidite solid-phase chemical synthesis in which the 3' ends of nucleic acid substrate sequences are covalently attached to a solid support, e.g., control pore glass. The 5' protecting groups can be, e.g., a triphenylmethyl group, such as dimethoxyltrityl (DMT) or monomethyoxytrityl; a carbonyl-containing group, such as 9-fluorenylmethyloxycarbonyl (FMOC) or levulinoyl; an acid-clearable group, such as pixyl; a fluoride-cleavable alkylsilyl group, such as tert-butyl dimethylsilyl (T-BD.MSi), triusopropyl silyl. or trimethylsilyl. The 3' protecting groups can be, e.g., β-cyanoethyl groups The trinucleotide synthesis format includes providing a substrate sequence having a 5' terminus and at least one base, both of which have protecting groups thereon. The 5' protecting group of the substrate sequence is then removed to provide a 5' deprotected substrate sequence, which is then coupled with a selected trinucleotide phosphoramidite sequence. The trinucleotide has a 3' terminus, a 5' terminus, and three bases, each of which has protecting groups thereon. The coupling step yields an extended oligonucleotide sequence. Thereafter, the removing and coupling steps are optionally repeated. When these steps are repeated, the extended oligonucleotide sequence yielded by each repeated coupling step becomes the substrate sequence of the next repeated removing step until a desired codon-varied oligonucleotide is obtained. This basic synthesis format can optionally include coupling together one or more of: mononucleotides, trinucleotide phosphoramidite sequences, and oligonucleotides.

The split-pool synthesis format includes providing substrate sequences, each having a 5' terminus and at least one base, both of which have protecting groups thereon. The 5' protecting groups of the substrate sequences are removed to provide 5' deprotected substrate sequences, which are then coupled with selected trinucleotide phosphoramidite sequences. Each trinucleotide has a 3' terminus, a 5' terminus, and three bases, all of which have protecting groups thereon. The coupling step yields extended oligonucleotide sequences. Thereafter, the removing and coupling steps are optionally repeated. When these steps are repeated, the extended oligonucleotide sequences yielded by each repeated coupling step become the substrate sequences of the next repeated removing step until extended intermediate oligonucleotide sequences are produced.

Additional steps of the split-pool format optionally include splitting the extended intermediate oligonucleotide sequences into two or more separate pools. After this is done, the 5' protecting groups of the extended intermediate oligonucleotide sequences are removed to provide 5' deprotected extended intermediate oligonucleotide sequences in the two or more separate pools. Following this, these 5' deprotected intermediates are coupled with one or more selected mononucleotides, trinucleotide phosphoramidite sequences, or oligonucleotides in the two or more separate pools to yield further extended intermediate oligonucleotide sequences. In turn, these further extended sequences are pooled into a single pool. Thereafter, the steps beginning with the removal of the 5' protecting groups of the substrate sequences to provide 5' deprotected substrate sequences are optionally repeated. When these steps are repeated, the further extended oligonucleotide sequences, yielded by each repeated coupling step that generates those specific sequences, become the substrate sequences of the next repeated removing step that includes those specific sequences until desired codon-varied oligonucleotides are obtained.

Both synthetic protocols described, supra, can optionally be performed in an automated synthesizer that automatically performs the steps. This aspect includes inputting character string information into a computer, the output of which then directs the automated synthesizer to perform the steps necessary to synthesize the desired codon-varied oligonucleotides.

Further details regarding tri-nucleotide synthesis are found in co-filed application U.S. Ser. No. 09/408393 "USE OF CODON VARIED OLIGONUCLEOTIDE SYNTHESIS FOR SYNTHETIC SHUFFLING" by Welch, et al. Attorney docket number 02-100700US.

TUNING NUCLEIC ACID RECOMBINATION USING OLIGONUCLEOTIDE-MEDIATED BLENDING

In one aspect, non-equimolar ratios of family shuffling oligonucleotides are used to bias recombination during the procedures noted herein. In this approach, equimolar ratios of family shuffling oligonucleotides in a set of family shuffling oligonucleotides are not used to produce a library of recombinant nucleic acids, as in certain other methods herein. Instead, ratios of particular oligonucleotides which correspond to the sequences of a selected member or selected set of members of the family of nucleic acids from which the family shuffling oligonucleotides are derived are selected by the practitioner.

Figure 2:
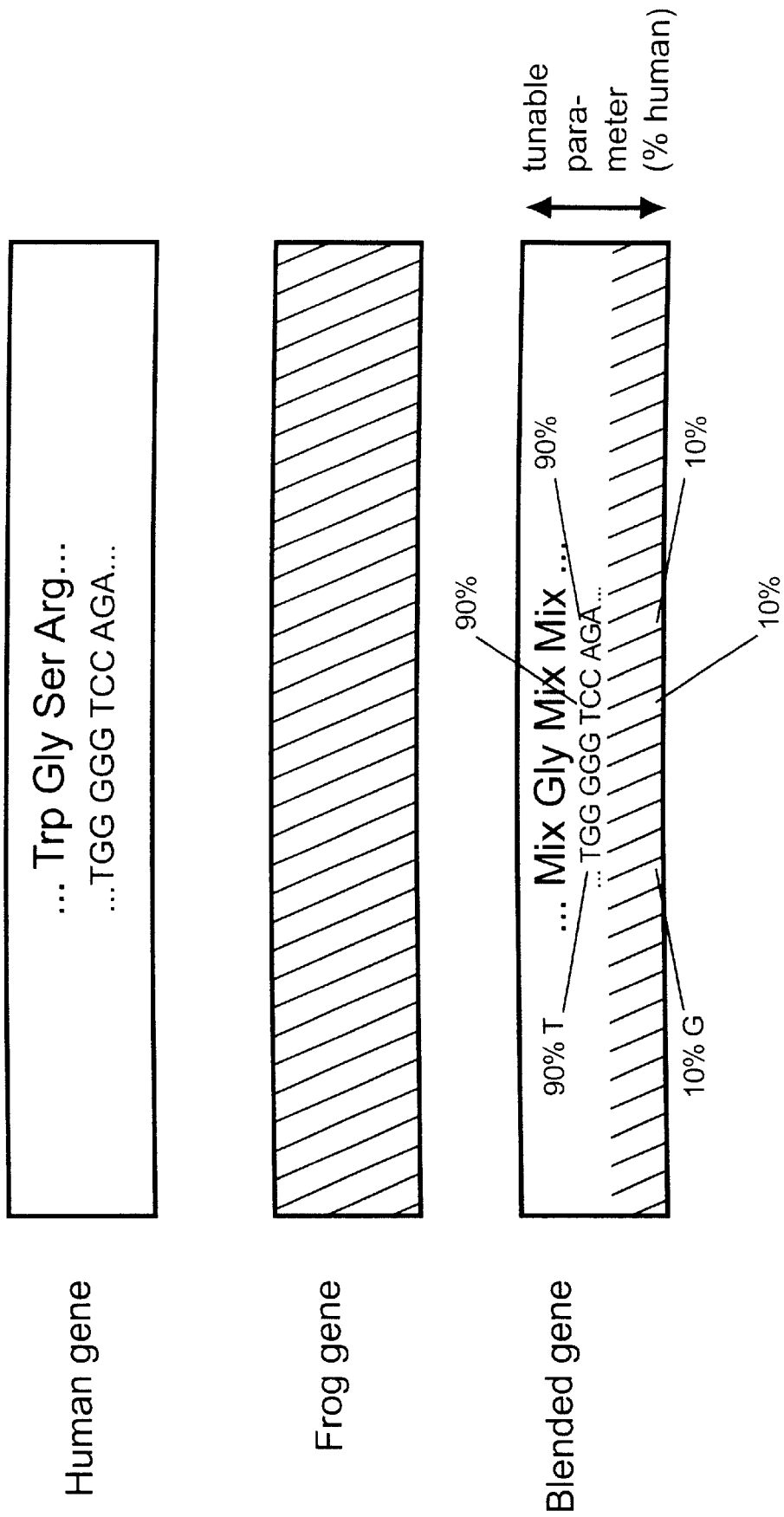
FIG. 2 (SEQ ID NO: 25 to 26 is a schematic of a low-homology shuffling procedure to provide for synthetic gene blending.

Thus, in one simple illustrative example, oligonucleotide mediated recombination as described herein is used to recombine, e.g., a frog gene and a human gene which are 50% identical. Family oligonucleotides are synthesized which encode both the human and the frog sequences at all polymorphic positions. However, rather than using an equimolar ratio of the human and frog derived oligonucleotides, the ratio is biased in favor of the gene that the user wishes to emulate most closely. For example, when generating a human-like gene, the ratio of oligonucleotides which correspond to the human sequence at polymorphic positions can be biased to greater than 50% (e.g., about 60%, 70%, 80%, or 90% or more of the oligos can correspond to the human sequence, with 40%, 30%, 20%, 1 00/, or less of the oligos corresponding to the frog sequence). Similarly, if one wants a frog-like gene, the ratio of oligonucleotides which correspond to the frog sequence at polymorphic positions can be biased to greater than 50%. In either case, the resulting "blended" gene (i.e., the resulting recombinant gene with characteristics of more than one parent gene) can then be recombined with gene family members which are closely related by sequence to the blended gene. Thus, in the case above, in the case where the ratio of oligonucleotides is selected to produce a more human-like blended gene, the blended gene is optionally further recombined with genes more closely similar to the original human gene. Similarly, where the ratio of oligonucleotides is selected to produce a more Frog-like blended gene, the blended gene is optionally further recombined with genes more closely similar to the original frog gene. This strategy is set out in FIG. 2. The strategy Is generally applicable to the recombination of any two or more nucleic acids by oligonucleotide mediated recombination.

Biasing can be accomplished in a variety of ways, including synthesizing disproportionate amounts of the relevant oligonucleotides, or simply supplying disproportionate amounts to the relevant gene synthesis method (e.g., to a PCR synthetic method as noted, supra).

As noted, this biasing approach can be applied to the recombination of any set of two or more related nucleic acids. Sequences do not have to be closely similar for selection to proceed. In fact, sequences do not even have to be detectably homologous for biasing to occur. In this case, "family" oligonucleotides are substituted for non-sequence homologous sets of oligonucleotides derived from consideration of structural similarity of the encoded proteins. For example, the immunoglobulin superfamily includes structurally similar members which display little or no detectable sequence homology (especially at the nucleic acid level). In these cases, non-homologous sequences are "aligned" by considering structural homology (e.g., by alignment of functionally similar peptide residues). A recombination space of interest can be defined which includes all permutations of the amino acid diversity represented by the alignment. The above biasing method is optionally used to blend the sequences with desired ratios of the nucleotides encoding relevant structurally similar amino acid sequences.

Any two or more sequences can be aligned by any algorithm or criteria of interest and the biasing method used to blend the sequences based upon any desired criteria. These include sequence homology, structural similarity, predicted structural similarity (based upon any similarity criteria which are specified), or the like. It can be applied to situations in which there is a structural core that is constant, but having many structural variations built around the core (for example, an 1g domain can be a structural core having many different loop lengths and conformations being attached to the core).

A general advantage to this approach as compared to standard gene recombination methods is that the overall sequence identity of two sequences to be blended can be lower than the identity necessary for recombination to occur by more standard methods. In addition, sometimes only selected regions are recombined, making it possible to take any structural or functional data which is available into account in specifying how the blended gene is constructed. Thus, sequence space which cannot be created by standard shuffling protocols is accessed by the blended gene and a higher percentage of active clones can sometimes be obtained if structural information is taken into consideration.

The general strategy above is applicable, e.g., to any set of genes with low sequence similarity. For example, there is a large family of TNF homologues whose sequence identity is in the range of about 30%, making standard shuffling protocols difficult to achieve. Of course, tuning recombination by selecting oligonucleotide proportions is also generally applicable to recombination of any two nucleic acids, including both high similarity homologues and low similarity homologues. Any alignment protocol can be selected to align two or more sequences and the resulting alignment can be used to create appropriate oligonucleotides to achieve recombination, and any biasing in the relative frequencies of sequences as compared to parental sequences can be achieved.

TARGETS FOR OLIGONUCLEOTIDE SHUFFLING

Essentially any nucleic acid can be shuffled by the oligonucleotide mediate methods herein. No attempt is made to identify the hundreds of thousands of known nucleic acids. As noted above, common sequence repositories for known proteins include GenBank EMBL, DDBJ and the NCBI. Other repositories can easily be identified by searching the internet.

One class of preferred targets for activation includes nucleic acids encoding therapeutic proteins such as erythropoietin (EPO), insulin, peptide hormones such as human growth hormone; growth factors and cytokines such as epithelial Neutrophil Activating Peptide-78, GROα/MGSA, GROβ, GROγ, MIP-1α, MIP-16, MCP-1, epidermal growth factor, fibroblast growth factor, hepatocyte growth factor, insulin-like growth factor, the interferons, the interleukins, keratinocyte growth factor, leukemia inhibitory factor, oncostatin M, PD-ECSF, PDGF, plelotropin, SCF, c-kit ligand, VEGEF, G-CSF etc. Many of these proteins are commercially available (See, e.g., the Sigma BioSciences 1997 catalogue and price list), and the corresponding genes are well-known.

Another class of preferred targets are transcriptional and expression activators. Example transcriptional and expression activators include genes and proteins that modulate cell growth, differentiation, regulation, or the like. Expression and transcriptional activators are found in prokaryotes, viruses, and eukaryotes, including fungi, plants, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA. Expression activators include cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Rnases such as Onconase and EDN are preferred targets for the synthetic methods herein, particularly those methods utilizing gene blending. One of skill will appreciate that both frog and human RNAses are known and are known to have a number of important pharmacological activities. Because of the evolutionary divergence between these genes, oligonucleotide-mediated recombination methods are particularly useful in recombining the nucleic acids.

Similarly, proteins from infectious organisms for possible vaccine applications, described in more detail below, including infectious fungi, e.g., Aspergillus, Candida species; bacteria, particularly E. coli, which serves a model for pathogenic bacteria, as well as medically important bacteria such as Staphylococci (e.g. aureus), Streptococci (e.g., pneumoniae), Clostridia (e.g., perfringens), Neisseria (e.g., gonorrhoea), Enterobacteriaceae (e.g., coli), Helicobacter (e.g., pylori), Vibrio (e.g., cholerae), Campylobacter (e.g., jejuni), Pseudomonas (e.g., aeruginosa), Haemophilus (e.g., influenzae), Bordetelia (e.g., pertussis), Mycoplasnia (e.g., pneumoniae), Ureaplasma (e.g., urealyticum), Legionella (e.g., pneumtiophilia), Spirochetes (e.g., Treponema, Leptospira, and Borrelia), Mycobacteria (e.g., tuberculosis, smegmatis), Actinomyces (e.g., israelii), Nocardia (e.g., asteroides), Chlamydia (e.g., trachomatis), Rickettsia, Coxiella, Ehrlichia, Rocholimaea, Brucella, Yersinia, Francisella, and Pasteurella; protozoa such as sporozoa (e.g., Plasmodia), rhizopods (e.g., Entamoeba) and flagellates (Trypanosoma, Leishmania, Trichomonas, Giardia, etc.); viruses such as (+) RNA viruses (examples include Poxviruses e.g., vaccinia; Picomaviruses, e.g. polio; Togaviruses, e.g., rubella; Flaviviruses, e.g., HCV; and Coronaviruses), (−) RNA viruses (examples include Rhabdoviruses, e.g., VSV; Paramyxovimses, e.g., RSV; Orthomyxovimses, e.g., influenza. Bunyaviruses; and Arenaviruses), dsDNA viruses (Reoviruses, for example), RNA to DNA viruses, i.e., Retroviruses, e.g., especially HIV and HTLV, and certain DNA to RNA viruses such as Hepatitis B virus.

Other proteins relevant to non-medical uses, such as inhibitors of transcription or toxins of crop pests e.g., insects, fungi, weed plants, and the like, are also preferred targets for oligonucleotide shuffling. Industrially important enzymes such as monooxygenases (e.g., p450s), proteases, nucleases, and lipases are also preferred targets. As an example, subtilisin can be evolved by shuffling family oligonucleotides for homologous forms of the gene for subtilisin. Von der Osten et al., *J. Biotechnol.* 28:55–68 (1993) provide an example subtilisin coding nucleic acid. Proteins which aid in folding such as the chaperonins are also preferred targets.

Preferred known genes suitable for oligonucleotide mediated shuffling also include the following: Alpha-1 antitrypsin, Angiostatin, Antihemolytic factor, Apolipoprotein, Apoprotein, Atrial natriuretic factor, Atrial natriuretic polypeptide, Atrial peptides, C-X-C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-I beta, RANTES, I309, R83915, R91733, HCC1, T58847, D31065, T64262), CD40 ligand, Collagen, Colony stimulating factor (CSF), Complement factor 5a, Complement inhibitor, Complement receptor 1, Factor IX, Factor VII, Factor VIII, Factor X, Fibrinogen, Fibronectin, Glucocerebrosidase, Gonadotropin, Hedgehog proteins (e.g., Sonic, Indian, Desert), Hemoglobin (for blood substitute; for radiosensitization), Hirudin, Human serum albumin, Lactoferrin, Luciferase, Neurturin, Neutrophil inhibitory factor (NIF), Osteogenic protein, Parathyroid hormone, Protein A, Protein G, Relaxin, Renin, Salmon calcitonin, Salmon growth hormone, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC I, SEC2, SEC3, SED, SEE), Toxic shock syndrome toxin (TSST-1), Exfoliating toxins A and B, Pyrogenic exotoxins A, B, and C, and M. arthritides mitogen, Superoxide dismutase, Thymosin alpha 1, Tissue plasminogen activator, Tumor necrosis factor beta (TNF beta), Tumor necrosis factor receptor (TNFR), Tumor necrosis factor-alpha (TNF alpha) and Urokinase.

Small proteins such as defensins (antifungal proteins of about 50 amino acids, EF40 (an anti fungal protein of 28 amino acids), peptide antibiotics, and peptide insecticidal proteins are also preferred targets and exist as families of related proteins. Nucleic acids encoding small proteins are particularly preferred targets, because conventional recombination methods provide only limited product sequence diversity. This is because conventional recombination methodology produces crossovers between homologous sequences about every 50–100 base pairs. This means that for very short recombination targets, crossovers occur by standard techniques about once per molecule. In contrast, the oligonucleotide shuffling formats herein provide for recombination of small nucleic acids, as the practitioner selects any "cross-over" desired.

DNA SHUFFLING AND GENE REASSEMBLY—HYBRID SYNTHETIC SHUFFLING METHODS

One aspect of the present invention is the ability to use family shuffling oligonucleotides and cross over oligonucleotides as recombination templates/intermediates in various DNA shuffling methods. In addition, nucleic acids made by the new synthetic techniques herein can be reshuffled by other available shuffling methodologies. A variety of such methods are known, including those taught by the inventors and their coworkers, e.g., Stemmer et al. (1994) "Rapid Evolution of a Protein" *Nature* 370:389–391; Stemmer (1994) "DNA Shuffling by Random Fragmentation and Reassembly: in vitro Recombination for Molecular Evolution." *Proc. Natl. Acad. USA* 91:10747–1075 1: Stemmer U.S. Pat. No. 5,603,793 METHODS FOR IN VITRO RECOMBINATION; Stemmer et al. U.S. Pat. No. 5,830,721 DNA MUTAGENESIS BY RANDOM FRAGMENTATION AND REASSEMBLY; Stemmer et al., U.S. Pat. No. 5,811,238 METHODS FOR GENERATING POLYNUCLEOTIDES HAVING DESIRED CHARACTERISTICS BY ITERATIVE SELECTION AND RECOMBINATION; Minshull et al., U.S. Pat. No. 5,837,458 METHODS AND COMPOSITIONS FOR CELLULAR AND METABOLIC ENGINEERING; Crameri et al. (1996), "Construction And Evolution Of Antibody-Phage Libraries By DNA Shuffling" *Nature Medicine* 2(1):100–103 describe antibody scuffling foc antibody phage libraries; WO95/22625; WO97/20078; WO96/33207; WO97/33957; WO98/27230; WO97/35966; WO98/31837; WO98/13487; WO98/13485; and WO989/42832. In addition, several applications describe important DNA shuffling methodologies, including Del Cardayre et al. 09/116,188 "EVOLUTION OF WHOLE CELLS AND ORGANISMS BY RECURSIVE SEQUENCE RECOMBINATION" filed 07–15–98 and Paten and Stemmer U.S. Ser. No. 60/102,362 SHUFFLING OF CODON ALTERED NUCLEIC ACIDS." These references also provide additional details on the process of hybridizing and elongating nucleic acids to achieve nucleic acid recombination.

In one aspect, a hybrid method which uses family gene shuffling in combination with more traditional recombination methods is used. For example, an active nucleic acid can be reassembled from oligonucleotides to have a few or even no homologous substitutions relative to a given target gene. The reassembled "backbone" nucleic acid is treated with DNase as in standard methods, and the resulting DNased fragments are spiked with family oligonucleotides comprising sequences corresponding to regions of sequence identity and diversity in a given nucleic acid. The nucleic acids are then reassembled into a library of homologous sequences by the methods below (e.g., PCR reassembly, or other reassembly methods). This procedure can result in an increase in the percentage of active clones which are found as compared to oligonucleotides synthetic methods which do not incorporate the use of a backbone nucleic acid.

A number of the publications of the inventors and their co-workers, as well as other investigators in the art describe techniques which facilitate DNA shuffling, e.g., by providing for reassembly of genes from small fragments, including oligonucleotides, as relevant to the present invention. In addition to the publications noted above and herein, Stemmer et al. (1998) U.S. Pat. No. 5,834,252 END COMPLEMENTARY POLYMERASE REACTION describe processes for amplifying and detecting a target sequence (e.g., in a mixture of nucleic acids), as well as for assembling large polynuclqotides from fragments. Crameri et al. (1998) *Nature* 391: 288–291 provides basic methodologies for gene reassembly, as does Crameri et al. (1998) Bio techniques 18(2): 194–196.

DNA SHUFFLING WITHOUT THE USE OF PCR

Although one preferred format for gene reassembly uses PCR, other formats are also useful. For example, site-directed or oligonucleotide-directed mutagenesis methods can be used to generate chimeras between 2 or more parental genes (whether homologous or non-homologous). In this regard, one aspect of the present invention relates to a new method of performing recombination between nucleic acids by ligation of libraries of oligonucleotides corresponding to the nucleic acids to be recombined.

In this format, a set of a plurality of oligonucleotides which includes a plurality of nucleic acid sequences from a plurality of the parental nucleic acids are ligated to produce a recombinant nucleic acid, typically encoding a full length protein (although ligation can also be used to make libraries of partial nucleic acid sequences which can then be recombined, e.g., to produce a partial or full-length recombinant nucleic acid). The oligonucleotide set typically includes at least a first oligonucleotide which is complementary to at least a first of the parental nucleic acids at a first region of sequence diversity and at least a second oligonucleotide which is complementary to at least a second of the parental nucleic acids at a second region of diversity. The parental nucleic acids can be homologous or non-homologous.

Often, nucleic acids are ligated with a ligase. In one typical format, the oligonucleotides are hybridized to a first parental nucleic acid which acts as a template, and ligated with a ligase. The oligos can also be extended with a polymerase and ligated. The polymerase can be, e.g., an ordinary DNA polymerase or a thermostable DNA polymerase. The ligase can also be an ordinary DNA ligase, or a thermostable DNA ligase. Many such polymerases and ligases are commercially available.

In one set of approaches, a common element for non-PCR based recombination methods is preparation of a single-stranded template to which primers are annealed and then elongated by a DNA polymerase in the presence of dNTP's and appropriate buffer. The gapped duplex can be sealed with ligase prior to transformation or electroporation into *E. coli*. The newly synthesized strand is replicated and generates a chimeric gene with contributions from the oligo in the context of the single-stranded (ss) parent.

For example, the ss template can.be prepared by incorporation of the phage IG region into a plasmid and use of a helper phage such as M13KO7 (Pharmacia Biotech) or R408 to package ss plasmids into filamentous phage particles. The ss template can also be generated by denaturation of a double-stranded template and annealing in the presence of the primers. The methods vary in the enrichment methods for isolation of the newly synthesized chimeric strand over the parental template strand. Isolation and selection of double stranded templates can be performed using available methods. See e.g., Ling et al. (1997) "Approaches to DNA mutagenesis: an overview." *Anal Biochem*. Dec 15;254(2):157–78; Dale et al. (1996) "Oligonucleotide-directed random mutagenesis using the phosphorothioate method" *Methods Mol Biol*. 57:369–74; Smith (1985) "In vitro mutagenesis" *Ann. Rev. Genet*. 19:423–462; Botstein & Shortle (1985) "Strategies and applications of in vitro mutagenesis" *Science* 229:1193–1201; and Carter (1986) "Site-directed mutagenesis" *Biochem J*. 237:1–7; Kunkel (1987) "The efficiency of oligonucleotide directed mutagenesis" *Nucleic Acids & Molecular Biology* (1987); Eckstein, F. and Lilley, D. M. J. eds Springer Verlag, Berlin.

For example, in one aspect, a "Kunkel style" method uses uracil containing templates. Similarly, the "Eckstein" method uses phosphorothioate-modified DNA (Taylor et al. (1985) "The use of phosphorothioate-modified DNA in restriction enzyme reactions to prepare nicked DNA." *Nucleic Acids Res*. 13:8749–8764; Taylor et al. (1985) "The rapid generation of oligonucleotide-directed mutations at high frequency using phosphorothioate-modified DNA" *Nucleic Acids Res*. 13:8765–8787; Nakamaye & Eckstein (1986) "Inhibition of restriction endonuclease Nci I cleavage by phosphorothioate groups and its application to oligonucleotide-directed mutageness." *Nucleic Acids Res*. 14: 9679–9698; Sayers et al. (1988). "Y-T Exonucleases in phosphorothioate-based oligonucleotide-directed mutagenesis." *Nucleic Acids Res*. 16:791–802; Sayers et al. (1988) "5'-3' Strand specific cleavage of phosphorothioate-containing DNA by reaction with restriction endonucleases in the presence of ethidium bromide" *Nucleic Acids Res*. 16:803–814). The use of restriction selection, or e.g., purification can be used in conjunction with mismatch repair deficient strains (see, e.g., Carter et al. (1985) "Improved oligonucleotide site directed mutagenesis using M13 vectors" *Nucleic Acids Res*. 13, 4431–4443 Carter (1 987) "Improved oligonucleotide-directed mutagenesis using M13 vectors." *Methods in Enzymol*. 154:382–403; Wells (1986) "Importance of hydrogen bond formation in stabilizing the transition state of subtilisin." *Trans. R. Soc. Lond*. A3 17, 415–423).

The "mutagenic" primer used in these methods can be a synthetic oligonucleotide encoding any type of randomization, insertion, deletion, family gene shuffling oligonucleotide based on sequence diversity of homologous genes, etc. The primer(s) could also be fragments of homologous genes that are annealed to the ss parent template. In this way chimeras between 2 or more parental genes can be generated.

Multiple primers can anneal to a given template and be extended to create multiply chimeric genes. The use of a DNA polymerase such as those from phages T4 or T7 are suitable for this purpose as they do not degrade or displace a downstream primer from the template.

For example, in one aspect, DNA shuffling is performed using uracil containing templates. In this embodiment, the gene of interest is cloned into an E. coli plasmid containing the filamentous phage intergenic (IG, ori) region. Single stranded (ss) plasmid DNA is packaged into phage particles upon infection with a helper phage such as M13KO7 (Pharmacia) or R408 and can be easily purified by methods such as phenol/chloroform extraction and ethanol precipitation. If this DNA is prepared in a dut- ung- strain of *E. coli*, a small number of uracil residues are incorporated into it in place of the normal thymine residues. One or more primers or other oligos as described above are annealed to the ss uracil-containing template by heating to 90° C. and slowly cooling to room temperature. An appropriate buffer containing all 4 deoxyribonucleotides, T7 DNA polymerase and T4 DNA ligase is added to the annealed template/primer mix and incubated between room temperature-37° C. for $\geq 1$ hour. The T7 DNA polymerase extends from the 3' end of the primer and synthesizes a complementary strand to the template incorporating the primer. DNA ligase seals the gap between the 3' end of the newly synthesized strand and the 5' end of the primer. If multiple primers are used, then the polymerase will extend to the next primer, stop and ligase will seal the gap. This reaction is then transformed into an ung+strain of E. coli and antibiotic selection for the plasmid is applied. The uracil N-glycosylase (ung gene product) enzyme in the host cell will recognize the uracil in the template strand and removes it, creating apyrimidinic sites that are either not replicated or the host repair systems will correct it by using the newly synthesized strand as a template. The resulting plasmids predominantly contain the desired change in the gene if interest. If multiple primers are used then it is possible to simultaneously introduce numerous changes in a single reaction. If the primers are derived from or correspond to fragments of homologous genes, then multiply chimeric genes can be generated.

CODON MODIFICATION

In one aspect, the oligonucleotides utilized in the methods herein have altered codon use as compared to the parental sequences from which the oligonucleotides are derived. In particular, it is useful, e.g., to modify codon preference to optimize expression in a cell in which a recombinant product of an oligonucleotide shuffling procedure is to be assessed or otherwise selected. Conforming a recombinant nucleic acid to the codon bias of a particular cell in which selection is to take place typically results in maximization of expression of the recombinant nucleic acid. Because the oligonucleotides used in the various strategies herein typically are made synthetically, selecting optimal codon preference is done simply by reference to well-known codon-bias tables. Codon-based synthetic methods as described supra are optionally used to modify codons in synthetic protocols.

In addition to the selection of oligonucleotide sequences to optimize expression, codon preference can also be used to increase sequence similarity between distantly related nucleic acids which are to be recombined. By selecting which codons are used in particular positions, it is possible to increase the similarity between the nucleic acids, which, in turn, increases the frequency of recombination between the nucleic acids. Additional details on codon modification procedures and their application to DNA shuffling are found in Paten and Stemmer, U.S. Ser. No. 60/102,362 "SHUFFLING OF CODON ALTERED NUCLEIC ACIDS," filed Sep. 29, 1998 and related application of Paten and Stemmer, Attorney docket number 018097-028510, entitled "SHUFFLING OF CODON ALTERED NUCLEIC ACIDS," filed Jan. 29, 1999.

LENGTH VARIATION BY MODULAR SHUFFLING

Many functional sequence domains for genes and gene elements are composed of functional subsequence domains. For example, promoter sequences are made up of a number of functional sequence elements which bind transcription factors, which, in turn, regulate gene expression. Enhancer elements can be combined with promoter elements to enhance expression of a given gene. Similarly, at least some exons represent modular domains of an encoded protein, and exons can be multimerized or deleted relative to a wild-type gene and the resulting nucleic acids recombined to provide libraries of altered gene (or encoded protein) modules (i.e., libraries of module inserted or deleted nucleic acids). The number and arrangement of modular sequences, as well as their sequence composition, can affect the overall activity of the promoter, exon, or other genetic module.

The concept of exons as modules of genes and encoded proteins is established, particularly for proteins which have developed in eukaryotes. See, e.g., Gilbert and Glynias (1993) Gene 137–144; Dolittle and Bork (October 1993) Scientific American 50–56; and Patthy (1991) Current Opinions in Structural Biology 1:351–361. Shuffling of exon modules is optimized by an understanding of exon shuffling rules. Introns (and consequently exons) occur in three different phases, depending on the splice junction of a codon at the exon-intron boundary. See, Stemmer (1995) Biotechnology 13:549–553; Patthy (1994) Current Opinions in Structural Biolopy 4:383–392 and Patthy (1991) Current Opinions in Structural Biology 1:351–361.

In nature, the splice junctions of shuffled exons have to be "phase compatible" with those of neighboring exons—if not, then a shift in reading frame occurs, eliminating the information of the exon module. The three possible phases of an intron are phases 1, 2, or 0, for the base position within the codon at the intron-exon boundary in which the intron occurs. Classification of introns according to their location relative to the reading frame is as follows: a phase 0 intron is located between two codons of flanking exons; a phase 1 intron is located between the first and second nucleotide of a codon and a phase 2 intron is located between the second and third nucleotide of a codon. Phase 1 introns are the most common in nature.

One aspect of the present invention is the shuffling of modular sequences (including, e.g., promoter elements and exons) to vary the sequence of such modules, the number of repeats of modules (from 0 (i.e. a deletion of the element) to a desired number of copies) and the length of the modules. In particular, standard shuffling methods, and/or the oligonucleotide mediated methods herein, can be combined with element duplication and length variation approaches simply by spiking appropriately designed fragments or oligonucleotides into a recombination mixture.

For example, a PCR-generated fragment containing the element to be repeated is spiked into a recombination reaction, with ends designed to be complementary, causing the creation of multimers in a subsequent recombination reaction. These multimers can be incorporated into final shuffled products by homologous recombination at the ends of the multimers, with the overall lengths of such multimers being dependent on the molar ratios of the modules to be multimerized. The rmultimers cai be made separately, or can be oligos in a gene reassmbly/recombination reaction as discussed supra.

In a preferred aspect, oligos are selected to generate multimers and/or to delete selected modules such as exons, promoter elements, enhancers, or the like during oligonucleotide recombination and gene assembly, thereby avoiding the need to make multimers or nucleic acids comprising module deletions separately. Thus, in one aspect, a set of overlapping family gene shuffling oligonucleotides is constructed to comprise oligos which provide for deletion or multimerization of sequence module elements. These "module shuffling" oligonucleotides can be used in conjunction with any of the other approaches herein to recombine homologous nucleic acids. Thus, sequence module elements are those subsequences of a given nucleic acid which provide an activity or distinct component of an activity of a selected nucleic acid, while module shuffling oligonucleotides are oligonucleotides which provide for insertion, deletion or multimerization of sequence modules. Examples of such oligonucleotides include those having subsequences corresponding to more than one sequence module (providing for deletion of intervening sequences and/or insertion of a module in a selected position), one or more oligonucleotides with ends that have regions of identity permitting multimerization of the one or more oligonucleotides (and, optionally, of associated sequences) during hybridization and elongation of a mixture of oligonucleotides, and the like.

Figure 3:
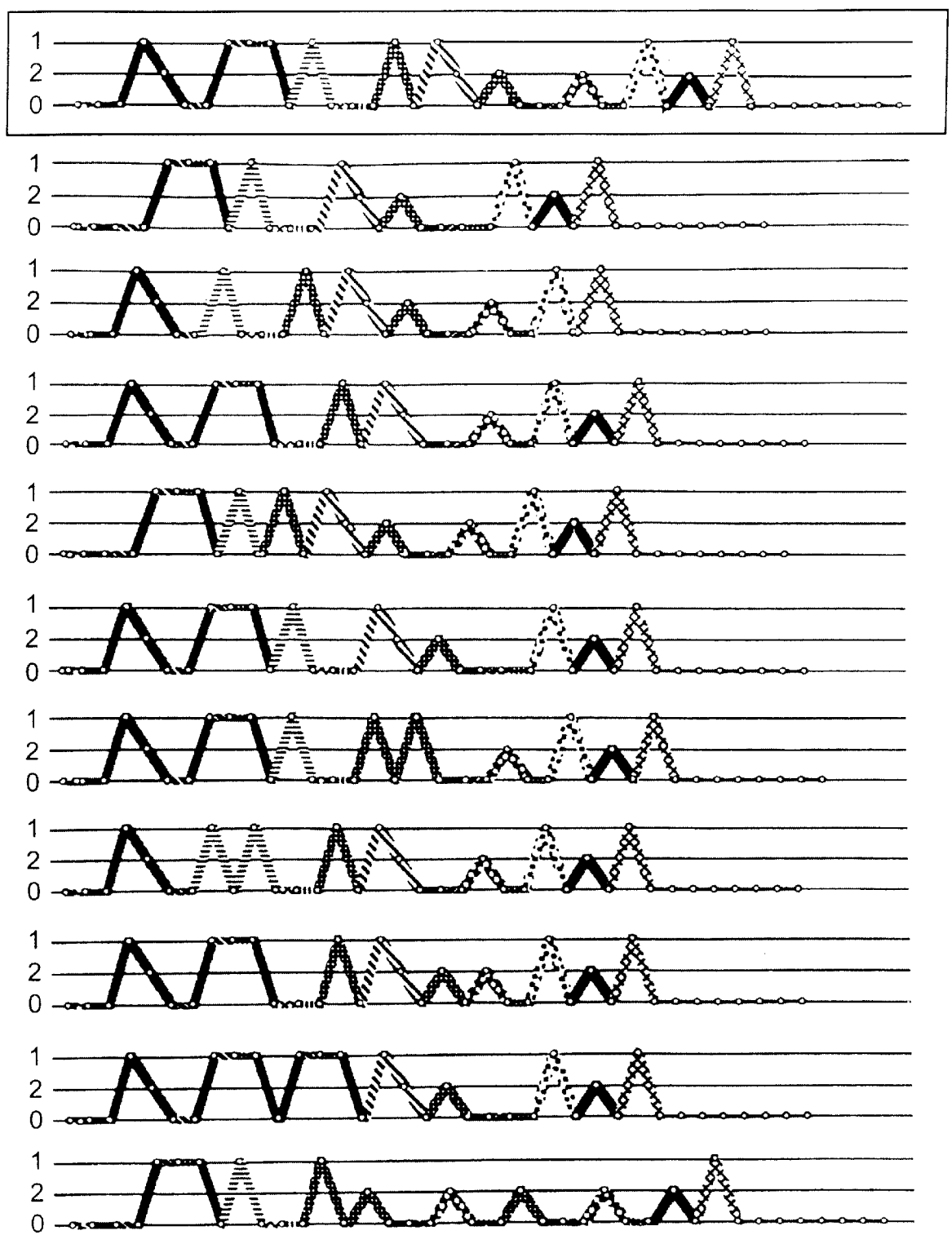
FIG. 3 is a schematic of a modular exon deletion/insertion library.

Libraries resulting from module deletion/insertion strategies noted above vary in the number of copies and arrangement of a given module relative to a corresponding or homologous parental nucleic acid. When the modules are exons, the oligonucleotides used in the recombination methods are typicalLy selected to result in exons being joined in the same phase (i.e., having the same reading frame) to increase the liklihood that any given library member will be functionally active. This is illustrated schematically in FIG. 3. The differently shaded modules represent separate exons, with the phase of the exon being indicated as 1, 2, or 0.

PROTEIN DOMAIN SHUFFLING

Family shuffling of genes is a good way to access functional diversity of encoded proteins. It can be advantageous, however, to shuffle only a portion of an encoded protein which provides an activity of interest particularly where the protein is multi functional and one or more activity can be mapped to a subsequence (a domain) of the overall protein.

For example, enzymes such as glycosyl transferases have two substrates: the acceptor and the activated sugar donor. To change the sugar to be transferred without altering the acceptor, it can be preferable to family shuffle only the sugar binding domain, since family shuffling the sugar acceptor domain can result in lowered numbers of the desired acceptor.

In one example, there are 5 enzymes, eA–eE (each of 500 amino acids) that transfers sugars a–-e to acceptors A–E. To generate a library of enzymes that transfer sugars a-e to acceptor A it can be preferable to shuffling the sugar binding domains of eA–eE, combining them with acceptor binding domains of eA.

One technical challenge in practicing this strategy is that there can be insufficient data to identify such functional domains in a protein of interest. When this is the case, a set of libraries can be generated by family shuffling random portions of the enzyme. For example, as applied to the family shuffling of enzymes eA–eE, above, a first library can be made encoding the first 100 amino acids of eA–eE, in combination with the last 400 amino acids of any one of eA–eE by appropriately selecting oligonucleotide sets for recombination and elongation. A second library can be made which family shuffles the second 100 amino acids of eA–eE, in combination with encoding the first 100 amino acids of any one of eA–Ae and the last 300 amino acids of any one of eA–Ae, and so on. Small subsets of these libraries are screened for a first desired function. Libraries that have retained the first desired function (e.g., acceptor activity in the example above) have a relatively higher proportion of variants in additional selectable fuinctions (e.g., sugar transfer in the example above).

This approach can be used for diversification of any multi-functional protein in which one property is desirably conserved. This strategy is particularly advantageous when the property to be conserved is complex (e.g., substrate specificity for, e.g., polyketides, non-ribosomal peptides or other natural products).

In general, selection of oligonucleotides to provide shuffling of individual domains (whether corresponding to known functional subsequences or to subsequences of unknown function as noted above) is performed by providing two general types of sequence-related oligonucleotides. The first type is provided by selecting sequence-related overlapping oligonucleotide sets corresponding to regions where recombination is desired (i.e., according to the strategies noted herein), while the second type provides recombination junctions between the domains to be shuffled and non-shuffled domains, i.e. similar to a crossover oligonucleotide as described herein. The non-shuffled domains can be produced by simple oligonucleotide gene reconstruction methods (e.g., using ligation or polymerase-mediated extension reactions to concatenate oligonucleotides), or the non-shuffled domains can be produced by enzymatic cleavage of larger nucleic acids.

EXPANDED FAMILY SHUFFLING INCORPORATING MOLECULAR MODELING AND ALANFNE SCANING

Family based oligo shuffling involves the recombination of homologous nucleic acids by making sets of family shuffling oligonucleotides which are recombined in gene synthesis and recombination protocols as discussed supra. As noted, the homologous nucleic acids can be natural or non-natural (i.e., artificial) homologues.

One advantage of recombining non-natural homologues is that sequence space other than naturally occurring sequence space is accessed by the resulting recombinant nucleic acids. This additional diversity allows for the development or acquisition of functional properties that are not provided by recombination of nucleic acids representing natural diversity.

The main disadvantage of creating random homologues for recombination is that many of the resulting homologues are not functional with respect to a relevant characteristic. For these homologues, much of the resulting increase in selectable sequence space is undesirable "noise" which has to be selected out of the population. In contrast, natural diversity represents evolutionarily tested molecules, representing a more targeted overall potential sequence space in which recombination occurs.

One way of capturing non-natural diversity without significantly increasing undesirable sequence space is to define those positions which can be modified in a given gene without significantly degrading the desired functional property of an encoded molecule (protein, RNA, etc.). At least two basic approaches to can be used.

First, point mutagenesis (e.g., alanine scanning) can be performed to define positions that can be mutated without a significant loss of function. In principle, all 20 amino acids could be tested at each position to define a large spectrum of point mutations that are essentially neutral with respect to function. Sets of shuffling oligos are then made which capture these non-natural (but still active) homologues. For many commercially important proteins, alanine scanning information is already available. For example, Young et al. (1997) *Protein Science* 6:1228–1236 describe alanine scanning of granulocyte colony stimulating factor (G-CSF).

Second, where structural information is available for a protein (and, e.g., how the protein interacts with a ligand), regions can be defined which are predicted to be mutable with little or no change in function. Sets of family shuffling oligos are then made which capture these non-natural (but still predicted to be active) homologues. A variety of protein crystal structures are available (including, e.g., the crystal structure of G-CSF: Hill et al. (1993) *PNAS* 90:5167).

Similarly, even where structural information is not available, molecular modeling can be preformed to provide a predicted stiucture, which can also be used to predict which residues can be changed without altering function. A variety of protein structure modeling programs are commercially available for predicting protein structure. Further, the relative tendencies of amino acids to form regions of superstructure (helixes, β-sheets, etc.) are well established. For example, O'Neil and DeGrado *Science* v.250 provide a discussion of the helix forming tendencies of the commonly occurring amino acids. Tables of relative structure forming activity for amino acids can be used as substitution tables to predict which residues can be functionally substituted in a given portion. Sets of family shuffling oligos are then made which capture these non-natural (but still predicted to be active) homologues.

POST-RECOMBINATION SCREENING TECHNIQUES

The precise screening method that is used in the various shuffling procedures herein is not a critical aspect of the invention. In general, one of skill can practice appropriate screening (i.e., selection) methods, by reference to the activity to be selected for.

In any case, one or more recombination cycle(s) is/are usually followed by one or more cycle of screening or selection for molecules or transformed cells or organisms having a desired property, trait or characteristic. If a recombination cycle is performed in vitro, the products of recombination, i.e., recombinant segments, are sometimes introduced into cells before the screening step. Recombinant segments can also be linked to an appropriate vector or other regulatory sequences before screening. Alternatively. products of recombination generated in vitro are sometimes packaged in viruses (e.g., bacteriophage) before screening. If recombination is performed in vivo, recombination products can sometimes be screened in the cells in which recombination occurred. In other applications, recombinant segments are extracted from the cells, and optionally packaged as viruses, before screening.

The nature of screening or selection depends on what property or characteristic is to be acquired or the property or characteristic for which improvement is sought, and many examples are discussed below. It is not usually necessary to understand the molecular basis by which particular products of recombination (recombinant segments) have acquired new or improved properties or characteristics relative to the starting substrates. For example, a gene can have many component sequences, each having a different intended role (e.g., coding sequence, regulatory sequences, targeting sequences, stability-conferring sequences, subunit sequences and sequences affecting integration). Each of these component sequences can be varied and recombined simultaneously. Screening/selection can then be performed, for example, for recombinant segments that have increased ability to confer activity upon a cell without the need to attribute such improvement to any of the individual component sequences of the vector.

Depending on the particular screening protocol used for a desired property, initial round(s) of screening can sometimes be performed using bacterial cells due to high transfection efficiencies and ease of culture. However, bacterial expression is often not practical or desired, and yeast, fungal or other eukaryotic systems are also used for library expression and screening. Similarly, other types of screening which are not amenable to screening in bacterial or simple eukaryotic library cells, are performed in cells selected for use in an environment close to that of their intended use. Final rounds of screening can be performed in the precise cell type of intended use.

If further improvement in a property is desired, at least one and usually a collection of recombinant segments surviving a first round of screening/selection are subject to a further round of recombination. These recombinant segments can be recombined with each other or with exogenous segments representing the original substrates or further variants thereof. Again, recombination can proceed in vitro or in vivo. If the previous screening step identifies desired recombinant segments as components of cells, the components can be subjected to fuirther recombination in vivo, or can be subjected to further recombination in vitro, or can be isolated before performing a round of in vitro recombination. Conversely, if the previous screening step identifies desired recombinant segments in naked form or as components of viruses, these segments can be introduced into cells to perform a round of in vivo recombination. The second round of recombination, irrespective how performed, generates further recombinant segments which encompass additional diversity than is present in recombinant segments resulting from previous rounds.

The second round of recombination can be followed by a further round of screening/selection according to the principles discussed above for the first round. The stringency of screening/selection can be increased between rounds. Also, the nature of the screen and the property being screened for can vary between rounds if improvement in more than one property is desired or if acquiring more than one new property is desired. Additional rounds of recombination and screening can then be performed until the recombinant segments have sufficiently evolved to acquire the desired new or improved property or function.

POST-SHUFFLING PROCEDURES

The nucleic acids produced by the methods of the invention are optionally cloned into cells for activity screening (or used in in vitro transcription reactions to make products which are screened). Furthermore, the nucleic acids can be sequenced, expressed, amplified in vitro or treated in any other common recombinant method.

General texts which describe molecular biological techniques useful herein, including mutagenesis, library construction, screening assays, cell culture and the like include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1–3, Cold Spring Harbor Laboratory, Cold Spring Harbor, N.Y., 1989 ("Sambrook") and *Current Protocols in Molecular Biology*, F.M. Ausubel et al., eds., Current Protocols, a joint venture between Greene Publishing Associates, Inc. and John Wiley & Sons, Inc., (supplemented through 1998) ("Ausubel")). Methods of transducing cells, including plant and animal cells, with nucleic acids are generally available, as are methods of expressing proteins encoded by such nucleic acids. In addition to Berger, Ausubel and Sambrook, useful general references for culture of animal cells include Freshney (*Culture of Animal Cells, a Manual of Basic Technique*, third edition Wiley—Liss, New York (1994)) and the references cited therein, Humason (*Animal Tissue Techniques*, fourth edition W.H. Freeman and Company (1979)) and Ricciardelli, et al., *In Vitro Cell Dev. Biol.* 25:1016–1024 (1989). References for plant cell cloning, culture and regeneration include Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg New York) (Gamborg). A variety of Cell culture media are described in.Atlas and Parks (eds) The Handbook of Microbiological Media (1993) CRC Press, Boca Raton, Fla. (Atlas). Additional information for plant cell culture is found in available commercial literature such as the *Life Science Research Cell Culture Catalogue* (1998) from Sigma-Aldrich, Inc (St Louis, Mo.) (Sigma-LSRCCC)

and, e.g., the Plant Culture Catalogue and supplement (1997) also from Sigma-Aldrich, Inc (St Louis, Mo.) (Sigma-PCCS).

Examples of techniques sufficient to direct persons of skill through in vitro amplification methods, useful e.g., for amplifying oligonucleotide shuffled nucleic acids including the polymerase chain reaction (PCR) the ligase chain reaction (LCR), Qβ-replicase amplification and other RNA polymerase mediated techniques (e.g., NASBA). These techniques are found in Berger, Sambrook, and Ausubel, id., as well as in Mullis et al., (1987) U.S. Patent No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&EN 36–47; *The Journal Of NIH Research* (1991) 3, 81–94; Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369: 684–685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra. In one preferred method, reassembled sequences are checked for incorporation of family gene shuffling oligonucleotides. This can be done by cloning and sequencing the nucleic acids, and/or by restriction digestion, e.g., as essentially taught in Sambrook, Berger and Ausubel, above. In addition, sequences can be PCR amplified and sequenced directly. Thus, in addition to, e.g., Sambrook, Berger, Ausubel and Innis (id. and above), additional PCR sequencing PCR sequencing methodologies are also particularly useful. For example, direct sequencing of PCR generated amplicons by selectively incorporating boronated nuclease resistant nucleotides into the amplicons during PCR and digestion of the amplicons with a nuclease to produce sized template fragments has been performed (Porter et al. (1997) *Nucleic Acids Research* 25(8) :1611–1617). In the methods, 4 PCR reactions on a template are performed, in each of which one of the nucleotide triphosphates in the PCR reaction mixture is partially substituted with a 2'deoxynucleoside 5'-[P-borano]-triphosphate. The boronated nucleotide is stochastically incorporated into PCR products at varying positions along the PCR amplicon in a nested set of PCR fragments of the template. An exonuclease which is blocked by incorporated boronated nucleotides is used to cleave the PCR amplicons. The cleaved amplicons are then separated by size using polyacrylamide gel electrophoresis, providing the sequence of the amplicon. An advantage of this method is that it uses fewer biochemical manipulations than performing standard Sanger-style sequencing of PCR amplicons.

IN SILICO SHUFFLING

"In silico" shuffling utilizes computer algorithms to perform "virtual" shuffling using genetic operators in a computer. As applied to the present invention, gene sequence strings are recombined in a computer system and desirable products are made, e.g., by reassembly PCR of synthetic oligonucleotides as described herein. In silico shuffling is described in detail in Selifonov and Stemmer "METHODS FOR MAKING CHARACTER STRINGS, POLYNUCLEOTIDES & POLYPEPTIDES HAVING DESIRED CHARACTERISTICS" filed Feb. 5, 1999, U.S. Ser. No. 60/118854.

In brief, genetic operators (algorithms which represent given genetic events such as point mutations, recombination of two strands of homologous nucleic acids, etc.) are used to model recombinational or mutational events which can occur in one or more nucleic acid, e.g., by aligning nucleic acid sequence strings (using standard alignment software, or by manual inspection and alignment) such as those representing homologous nucleic acids and predicting recombinational outcomes. The predicted recombinational outcomes are used to produce corresponding molecules, e.g., by oligonucleotide synthesis and reassembly PCR.

INTEGRATED ASSAYS AND INTEGRATED SYSTEM ELEMENTS

As noted throughout, one preferred aspect of the present invention is the alignment of nucleic acids using a computer and sequence alignment software. Similarly, computers having appropriate software can be used to perform "in silico" shuffling prior to physical oligonucleotide synthesis. In addition, other important integrated system components can provide for high-throughput screening assays, as well as the coupling of such assays to oligonucleotide selection, synthesis and recombination.

Of course, the relevant assay will depend on the application. Many assays for proteins, receptors, ligands and the like are known. Formats include binding to immobilized components, cell or organismal viability, production of reporter compositions, and the like.

In the high throughput assays of the invention, it is possible to screen up to several thousand different shuffled variants in a single day. In particular, each well of a microtiter plate can be used to run a separate assay, or, if concentration or incubation time effects are to be observed, every 5–10 wells can test a single variant. Thus, a single standard microtiter plate can assay about 100 (e.g., 96) reactions. If 1536 well plates are used, then a single plate can easily assay from about 100- about 1500 different reactions. It is possible to assay several different plates per day; assay screens for up to about 6,000–20,000 different assays (i.e., involving different nucleic acids, encoded proteins, concentrations, etc.) is possible using the integrated systems of the invention. More recently, microfluidic approaches to reagent manipulation have been developed, e.g., by Caliper Technologies (Mountain View, Calif.).

In one aspect, library members, e.g., cells, viral plaques, spores or the like, are separated on solid media to produce individual colonies (or plaques). Using an automated colony picker (e.g., the Q-bot, Genetix, U.K.), colonies or plaques are identified, picked, and up to 10,000 different mutants inoculated into 96 well microtiter dishes containing two 3 mm glass balls/well. The Q-bot does not pick an entire colony but rather inserts a pin through the center of the colony and exits with a small sampling of cells, (or mycelia) and spores (or viruses in plaque applications). The time the pin is in the colony, the number of dips to inoculate the culture medium, and the time the pin is in that medium each effect inoculum size, and each can be controlled and optimized. The uniform process of the Q-bot decreases human handling error and increases the rate of establishing cultures (roughly 10,000/4 hours). These cultures are then shaken in a temperature and humidity controlled incubator. The glass balls in the microtiter plates act to promote uniform aeration of cells and the dispersal of mycelial fragments similar to the blades of a fermenter. Clones from cultures of interest can be cloned by limiting dilution. As also described supra, plaques or cells constituting libraries can also be screened directly for production of proteins, either by detecting hybridization, protein activity, protein binding to antibodies, or the like.

A number of well known robotic systems have also been developed for solution phase chemistries useful in assay systems. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a scientist. Any of the above devices are suitable for use with the present invention, e.g., for high-throughput screening of molecules assembled from the various oligonucleotide sets described herein. The nature and implementation of modifications to these devices (if any) so that they can operate as discussed herein with reference to the integrated system will be apparent to persons skilled in the relevant art.

High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

Optical images viewed (and, optionally, recorded) by a camera or other recording device (e.g., a photodiode and data-storage device) are optionally further processed in any of the embodiments herein, e.g., by digitizing the image and/or storing and analyzing the image on a computer. A variety of commercially available peripheral equipment and software is available for digitizing, storing and analyzing a digitized video or digitized optical image, e.g., using PC (Intel x86 or Pentium chip- compatible DOS™, OS2# WINDOWS™, WINDOWS NT™ or WINDOWS95™ based machines), MACINTOSH™, or UNIX based (e.g., SUN™ work station) computers. One conventional system carries light from the assay device to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

Integrated systems for assay analysis in the present invention typically include a digital computer with sequence alignment software and one or more of: high-throughput liquid control software, image analysis software, data interpretation software, and the like.

A robotic liquid control armature for transferring solutions from a source to a destination can be operably linked to the digital computer and an input device (e.g., a computer keyboard) can be used for entering data to the digital computer to control high throughput liquid transfer, oligonucleotide synthesis and the like, e.g., by the robotic liquid control armature. An image scanner can be used for digitizing label signals from labeled assay component. The image scanner interfaces with the image analysis software to provide a measurement of probe label intensity.

Of course, these assay systems can also include integrated systems incorporating oligonucleotide selection elements, such as a computer, database with nucleic acid sequences of interest, sequence alignment software, and oligonucleotide selection software. In addition, this software can include components for ordering the selected oligonucleotides, and/or directing synthesis of oligonucleotides by an operably linked oligonucleotide synthesis machine. Thus, the integrated system elements of the invention optionally include any of the above components to facilitate high throughput recombination and selection. It will be appreciated that these high-throughput recombination elements can be in systems separate from those for performing selection assays, or the two can be integrated.

In one aspect, the present invention comprises a computer or computer readable medium with an instruction set for selecting an oligonucleotide set such as a set of family shuffling oligonucleotides using the methods described herein. The instruction set aligns homologous nucleic acids to identify regions of similarity and regions of diversity (e.g., as in typical alignment software such as BLAST) and then selects a set of overlapping oligonucleotides that encompass the regions of similarity and diversity, optionally using any of the weighting factors described herein (e.g., predominant selection of oligonucleotides corresponding to one or more nucleic acid to be recombined, as in the gene blending methods herein). The computer or computer readable medium optionally comprises features facilitating use by a user, e.g., an input field for inputting oligonucleotide selections by the user, a display output system for controlling a user-viewable output (e.g., a GUI). an output file which directs synthesis of the oligonucleotides, e.g., in an automated synthesizer, and the like.

EXAMPLE

Betalactamase Shuffling With Three Bridging Oligos

In this example, two beta lactamase genes (CFAMPC and FOX) were shuffled using three bridging oligonucleotides. The oligos were as follows: (SEQ ID NOS 1–3, respectively, in order of appearance).

1) CAAATACTGGCCGGAACTGAAAGGTTCT-GCTTTCGACGGT

2) GTCGTGTTCTGCAGCCGCTGGGTCTG-CACCACACCTACAT

3) TCGTTACTGGCGTATCGGTGACATGAC-CCAGGGTCTGGGT

The recombination reaction was performed using 2 micrograms of DNAsed fragments from CFAMPC and FOX. All three oligos were added to the reaction 1:1 in a total of 60 microliters of 1× Taq-mix (7070 microliters of $H_2O$, 100 microliters Taq buffer, 600 microliters $MgCl_2$ (25 mM), 80 microliters dNTPs (100 mM)).

Reactions were performed with 150 ng primers (2× molar), 750 ng primers (10× molar), and 1500 ng primers (20× molar). 20 microliters of the assembling mix were added to 60 microliters of the 1× Taq mix and 40 thermal cycles were performed at 94° C. (30 sec.) 40° C. (30 sec) and 72° C. (30 sec). 1, 2, 4, and 8 microliters of the resulting products were then PCR amplified for 40 cycles (same thermal cycling conditions as before) using primers for the end regions of the betalactamase genes. The resulting material was then digested with Sfi overnight at 50° C., gel purified and ligated into vector Sfi-BLA-Sfi (MG18), transformed into TGI and plated on Tet 20. 50 colonies were selected from the Tet 20 plates and amplified by colony PCR. The PCR amplicon was then digested overnight-at 37° C. with HinFl. Restriciton analysis revealed that 2 wt sequences for each parental gene, as well as 7 different recombinant products (for the 10× molar reaction) or 8 different clones (for the 20× reaction) were produced.

EXAMPLE

Creating Semisinthetic Library By Oligo Spiking

Genes to be used are cry 2Aa, cry2Ab, and cry2Ac. DNA aligment was done with DNA star using editseq. and megalig. Oligos are 50 umol synthesis (BRL, Liftech.) Oligos for the region between Amino acid 260–630 are designed for cry2Ac in regard to diversity of this region. Oligos are resuspended in 200 ul H$_2$O. The oligos are as follows: (SEQ ID NOS 4–22, respectively, in order of appearance).

CRY2-1 TGGTCGTTATTTAAATATCAAAGCCT-TCTAGTATCTTCCGGCGCTAATYTATATGC

CRY2-2 CGGCGCTAATTTATATGCGAGTGG-TAGTGGTCCAACACAATCATTTACAGCACA

CRY2-3 CTAATTATGTATTAAATGGTTTGAGTG-GTGCTAGGACCACCATTACTTTC CCTAATATT

CRY2-4 CTTTCCCTAATATTGGTGGTCTTC-CCGTCTACCACAACTCAACATTGCATTTTG CGAGG

CRY2-5 AGGATTAATTATAGAGGTGGAGTGT-CATCTAGCCGCATAGGTCAAGCTAATCT

CRY2-6 CTAATCTTAATCAAAACTTTAACATTTC-CACACTTTTCAATCCTTTACAAA CACCGTTT

CRY2-7 TTTATTAGAAGTTGGCTAGATTCTGGTA-CAGATCGGGAAGGCGTTGCCACCTCTAC

CRY2-8 TGCCACCTCTACAAACTGGCAATCAG-GAGCCTTTGAGACAACTTTATTA

CRY2-9 0 ACAACTTTATTACGATTTAGCATTTM-CAGCTCGTGGTAATTCGAACTTTTTCCCA

CRY2-10 TCCGTAATATTTCTGGTGTTGTTGGGAC-TATTAGCAACGCAGATT AGCAAG ACCTCTAC

CRY2-11 ACTTTAATGAAATAAGAGATATAGGAAC-GACAGCAGTCGCTAGCCTTGT AACAGTGCATA

CRY2-12 TAATATCTATGACACTCATGAAAATGG-TACTATGATTCATTTAGCGCCAAA TGACTATAC

CRY2-13 TATACAGGA TTACCGTATCTCCAATA-CATGCCACTCAAGTAAATAATC AAATTCGAAC

CRY2-14 CAAATTCGAACGTTATTTC-CGAAAAATATGGTAATCAGGGTGATTCCTT GAGATTTGA

CRY2-15 AGATTTGAGCTAAGCAACCCAACG-GCTCGATACACACTFAGAGGGAA TGGAAAT-AGTTAC

CRY2-16 AGAGTATCTTCAATAGGAAGTFCCA-CAATTCGAGTFACTA

CRY2 17 CTGCAAATGTTAATACTACCA-CAAATAATGATGGAGTACTTGATAATGG AGCTCGTTTTT

CRY2-18 TATCGGTAATGTAGTGGCAAGT-GCTAATACTAATGTACCATTAGATATACA AGT-GACATT

CRY2-19 ATACAAGTGACATTTAACGGCAATCCA-CAATTTGAGCTTATGAATATTATG TGTTCCA

Family shuffling is done as described in Crameri et al. (1995) Nature 391: 288–291, except that oligos are spiked into the assembling mix as described in Crameri et al. (1998) Bio techniques 18(2): 194–196. The PCR reactions with outside primer 1 for (SEQ ID NO:23) ATGAATAATGTAT-TGAATA and 1 rev TTAATAAAGTGGTGGAAGATT (SEQ ID NO:24)are done with Taq/Pfu (9:1) mix (Taq from Qiagen, Pfu from Stratagene) PCR program 96° C. (30 sec). 50° C. (30sec). 72° C. (1 min) for 25 cycles. The reaction is diluted 10x and an additional cycle is performed. The gene is ligated into a vector and transformed into TG1 competent Cells, and plated on LB+Amp100 plates. Single colonies are picked for colony PCR and then analyzed by restriction digestion.

EXAMPLE

Oligo Shuffling of Libraries

An advantage of oligonucleotide mediated shuffling methods is the ability to recombine nucleic acids between libraries of oligos generated for a number of different sites in a gene of interest. Generating libraries with complex combinations of randomizations in different regions of a target gene is facilitated by oligonucleotide mediated shuffling approaches.

For example, the antigen-binding site of an antibody or antibody fragment such as a single-chain Fv (ScFv), or Fab is mainly comprised of 6 complementarity-determining regions (CDR's). These CDR's are present on one face of the properly folded molecule, but are separated in the linear gene sequence. Synthetic oligonucleotides or those generated by PCR of one or more antibody genes can be used to generate sequence diversity at individual CDR's. This process can be repeated with a second CDR, then a third, until a library of diverse antibodies is formed. DNA shuffling formats have a distinct advantage that allow for libraries of each CDR to be generated simultaneously and inter-CDR recombination events will frequently occur to potentially generate all possible combinations of different CDR's. Recursive DNA shuffling and screening for an improved trait or property can be used to optimize protein function.

Similarly, the 3-dimensional structures of many cytokines share a common 4-helix bundle structure with long connecting loops. The receptor binding sites for some of these proteins has been determined and is localized to 2 or more regions of the protein that are separate in the linear gene sequence. Modeling of related proteins could be used to predict functional regions of unknown proteins for targeting libraries. Libraries in each of these regions can be generated using synthetic oligos, family-shuffling oligos, fragments of homologous genes, or combinations thereof as herein. Oligonucleotide mediated shuffling allows one to generate libraries in each of these regions simultaneously and to generate recombinants between each library. In this way, combinations between members of each library can be screened for improved function. Those isolates with improved function can then be submitted to successive rounds of DNA shuffling. In this way, isolates with the highest activity in each library and potential synergies between members of different libraries can be selected.

Other methods that optimize each library independently may fail to isolate such synergistic interactions.

Another example is the shuffling of enzymes where the active site and substrate binding site(s) is comprised of residues close together in the 3-dimensional structure of the folded protein, but separated in the linear sequence of the gene. DNA shuffling can simultaneously generate libraries in each region that interact with substrate. DNA shuffling also allows all possible combinations of changes between each library to be generated and can be evaluated for an improved trait or property.

Modifications can be made to the method and materials as hereinbefore described without departing from the spirit or scope of the invention as claimed, and the invention can be put to a number of different uses, including:

The use of an integrated system to select family shuffling oligonucleotides (e.g., by a process which includes sequence alignment of parental nucleic acids) and to test shuffled nucleic acids for activity, including in an iterative process.

An assay, kit or system utilizing a use of any one of the selection strategies, materials, components, methods or substrates hereinbefore described. Kits will optionally additionally comprise instructions for performing methods or assays, packaging materials, one or more containers which contain assay, device or system components, or the like.

In an additional aspect, the present invention provides kits embodying the methods and apparatus herein. Kits of the invention optionally comprise one or more of the following: (1) a recombination component as described herein; (2) instructions for practicing the methods described herein, and/or for operating the oligonucleotide synthesis or assembled gene selection procedures herein; (3) one or more assay component; (4) a container for holding nucleic acids or enzymes, other nucleic acids, transgenic plants, animals, cells, or the like (5) packaging materials, and (6) a computer or computer readable medium having instruction sets for aligning target nucleic acids and for selecting oligonucleotides which, upon hybridization and elongation, will result in shuffled forms of the target nucleic acids.

In a further aspect, the present invention provides for the use of any component or kit herein, for the practice of any method or assay herein, and/or for the use of any apparatus or kit to practice any assay or method herein.

While the foregoing invention has been described in some detail for purposes of clarity and understanding, it will be clear to one skilled in the art from a reading of this disclosure that various changes in form and detail can be made without departing from the true scope of the invention. For example, all the techniques and materials described above can be used in various combinations. All publications and patent documents cited in this application are incorporated by reference in their entirety for all purposes to the same extent as if each individual publication or patent document were so individually denoted.

What is claimed is:

1. A composition, comprising:
  a set of nucleic acids, comprising:
    a first subset of chemically synthesized oligonucleotide members which collectively correspond to at least a substantial portion of a first target nucleic acid; and,
    a second subset of chemically synthesized oligonucleotide members which collectively correspond to at least a substantial portion of a second target nucleic acid;
    wherein the first and second target nucleic acids encode non-identical proteins and comprise a plurality of regions of difference, and
    wherein the first and second subsets of chemically synthesized oligonucleotide members correspond to the regions of difference, and the first and second subsets are present in substantially non-equimolar amounts.

2. The composition of claim 1, wherein the members of the first subset which correspond to the regions of difference are present in the composition at a ratio of about 60 percent to about 40 percent members of the second set which correspond to the regions of difference, or higher.

3. The composition of claim 1, wherein the plurality of regions of difference comprise a plurality of non-overlapping subsequence regions of the first or second target nucleic acid.

4. The composition of claim 1, wherein the members of the first or second subsets each have a sequence or subsequence identical to at least one subsequence from at least one of the selected target sequences.

5. The composition of claim 1, wherein the members of the first or second subsets comprise a plurality of homologous oligonucleotides corresponding to a plurality of regions of homology between the first and second target sequences, wherein each of the plurality of homologous oligonucleotides comprise at least one variant subsequence.

6. The composition of claim 1, further comprising one or more of: a polymerase, a thermostable DNA polymerase, a nucleic acid synthesis reagent, a buffer, a salt, magnesium, Taq polymerase, Klenow polymerase, dATP, dTTP, dGTP, dCTP, or one or more nucleic acid comprising one or more of the plurality of members of the selected set of homologous target sequences.

7. The composition of claim 1, wherein the set of nucleic acids is provided to the composition by aligning a plurality of homologous target sequences, determining at least one region of identity and at least one region of variance and synthesizing the set of oligonucleotides to encode at least a portion of the at least one region of identity, or at least a portion of the at least one region of variance, or at least a portion of both the at least one region of identity and the at least one region of variance.

8. The composition of claim 1, wherein the set of nucleic acids comprises a plurality of members collectively comprising at least 5 sequence diversity domains.

9. The composition of claim 1, wherein the set of nucleic acids comprises 10 or more sequence diversity domains.

10. The composition of claim 1, wherein the set of nucleic acids comprises a set of crossover family diversity oligonucleotides, each comprising a plurality of sequence a diversity domains, with at least a first of the sequence diversity domains corresponding to the first target nucleic acid and a second of the diversity domains corresponding to the second target nucleic acid.

11. The composition of claim 9, wherein the sequence diversity domains correspond to adjacent sequence regions on the first and second target nucleic acids when sequences corresponding to the target nucleic acids are aligned.

12. The composition of claim 1, wherein the oligonucleotide members of the first subset which correspond to the regions of difference are present in the composition at a ratio of about 70 percent to about 30 percent members of the second set which correspond to the regions of difference, or higher.

13. The composition of claim 1, wherein the oligonucleotide members of the first subset which correspond to the regions of difference are present in the composition at a ratio of about 80 percent to about 20 percent members of the second set which correspond to the regions of difference, or higher.

14. The composition of claim 1, wherein the oligonucleotide members of the first subset which correspond to the regions of difference are present in the composition at a ratio of about 90 percent to about 10 percent members of the second set which correspond to the regions of difference, or higher.

15. The composition of claim 1, wherein the first and second sets of oligonucleotides together comprise a plurality of members collectively comprising at least 10 sequence diversity domains.

16. The composition of claim 1, wherein the first and second sets of oligonucleotides together comprise a plurality of members collectively comprising at least 20 sequence diversity domains.

17. The composition of claim 1, wherein the first and second sets of oligonucleotides together comprise a plurality of members collectively comprising at least 50 sequence diversity domains.

18. The composition of claim 1, wherein the first and second sets of oligonucleotides together comprise a plurality of members collectively comprising at least 75 sequence diversity domains.

19. The composition of claim 1, wherein the first and second sets of oligonucleotides together comprise a plurality of members collectively comprising at least 100 sequence diversity domains.

20. The composition of claim 1, wherein the first or second subset is present at a molar ratio of 50% or greater of the set of nucleic acids.

21. The composition of claim 1, wherein the first or second subset is present at a molar ratio of 60% or greater of the set of nucleic acids.

22. The composition of claim 1, wherein the first or second subset is present at a molar ratio of 70% or greater of the set of nucleic acids.

23. The composition of claim 1, wherein the first or second subset is present at a molar ratio of 80% or greater of the set of nucleic acids.

24. The composition of claim 1, wherein the first or second subset is present at a molar ratio of 90% or greater of the set of nucleic acids.

25. A composition, comprising:
  a set of nucleic acids, comprising:
    a first subset of chemically synthesized oligonucleotide members which collectively correspond to at least a substantial portion of a first target nucleic acid;
    a second subset of chemically synthesized oligonucleotide members which collectively correspond to at least a substantial portion of a second target nucleic acid;
    wherein the first and second target nucleic acids comprise a plurality of regions of difference, the first and second subsets of oligonucleotide members correspond to the regions of difference, and the first and second subsets are present in substantially non-equimolar amounts; and
    a third subset of chemically sythesized oligonucleotide members which collectively correspond to all or a substantial portion of a third target member, which third subset is present in the composition in an amount that is substantially non-equimolar as compared to the first or second subsets.

26. The composition of claim 25, wherein the first, second or third subset is present at a molar ratio of 50% or greater of the overall set of nucleic acids.

27. The composition of claim 25, wherein the first, second or third subset is present at a molar ratio of 60% or greater of the overall set of nucleic acids.

28. The composition of claim 25, wherein the first, second or third subset is present at a molar ratio of 70% or greater of the overall set of nucleic acids.

29. The composition of claim 25, wherein the first, second or third subset is present at a molar ratio of 80% or greater of the overall set of nucleic acids.

30. The composition of claim 25, wherein the first, second or third subset is present at a molar ratio of 90% or greater of the overall set of nucleic acids.

31. The composition of claim 1, wherein the first and second target nucleic acids are 50% or more identical in sequence when aligned for maximum correspondence.

32. The composition of claim 1, wherein the first and second target nucleic acids are 80% or more identical in sequence when aligned for maximum correspondence.

33. The composition of claim 1, wherein the first and second target nucleic acids are 90% or more identical in sequence when aligned for maximum correspondence.

34. The composition of claim 1, wherein the first and second target nucleic acids are 95% or more identical in sequence when aligned for maximum correspondence.

35. The composition of claim 1, wherein the members of the first and second subset are substantially similar in length.

36. The composition of claim 35, wherein the members of the first and second subset are about 20 or more nucleotides in length.

37. The composition of claim 35, wherein the members of the first and second subset are about 30 or more nucleotides in length.

38. The composition of claim 35, wherein the members of the first and second subset are about 40 or more nucleotides in length.

39. The composition of claim 35, wherein the members of the first and second subset are about 50 or more nucleotides in length.

40. The composition of claim 35, wherein the members of the first and second subset are about 60 or more nucleotides in length.

41. The composition of claim 35, wherein the members of the first and second subset are about 70 or more nucleotides in length.

42. The composition of claim 35, wherein the members of the first and second subset are about 80 or more nucleotides in length.

43. The composition of claim 35, wherein the members of the first and second subset are about 90 or more nucleotides in length.

44. The composition of claim 35, wherein the members of the first and second subset are about 100 or more nucleotides in length.

45. The composition of claim 1, wherein the members of the first or second subsets comprise overlapping oligonucleotide members.

46. The composition of claim 45, wherein the members of the first or second subsets overlap by about 5 or more bases.

47. The composition of claim 45, wherein the members of the first or second subsets overlap by about 10 or more bases.

48. The composition of claim 45, wherein the members of the first or second subsets overlap by about 20 or more bases.

49. A composition, comprising:
a set of nucleic acids, comprising:
a first subset of chemically synthesized oligonucleotide members which collectively correspond to at least a substantial portion of a first target nucleic acid;
a second subset of chemically synthesized oligonucleotide members which collectively correspond to at least a substantial portion of a second target nucleic acid;
wherein the first and second target nucleic acids comprise a plurality of regions of difference, the first and second subsets of oligonucleotide or nucleic acid fragment members correspond to the regions of difference, and the first and second subsets are present in substantially non-equimolar amounts; and,
wherein the first subset comprises a first oligonucleotide corresponding to at least one of the regions of difference, and wherein the second subset comprises a second oligonucleotide corresponding to the at least one region of difference, wherein the first and second oligonucleotides comprise subsequences of identity flanking a subsequence of difference.

50. The composition of claim 49, wherein at least one of the subsequences of identity is 5 or more nucleotides in length.

51. The composition of claim 49, wherein at least one of the subsequences of identity is 10 or more residues in length.

52. The composition of claim 49, wherein at least one of the subsequences of identity is 15 or more residues in length.

53. The composition of claim 49, wherein at least one of the subsequences of identity is 20 or more residues in length.

54. The composition of claim 49, wherein at least one of the subsequences of identity is 50 or more residues in length.

55. The composition of claim 1, wherein the set of nucleic acids comprises one or more chimeraplasts.

56. The composition of claim 1, wherein the set of nucleic acids comprises one or more DNA oligonucleotides.

57. The composition of claim 1, wherein the set of nucleic acids comprises one or more oligonucleotide that comprises one or more non-standard nucleotide.

58. The composition of claim 1, wherein the set of nucleic acids comprises one or more oligonucleotide that comprises one or more methylated nucleotide.

59. A composition, comprising:
a set of nucleic acids, comprising:
a first subset of chemically synthesized oligonucleotide members which collectively correspond to at least a substantial portion of a first target nucleic acid;
a second subset of chemically synthesized oligonucleotide members which collectively correspond to at least a substantial portion of a second target nucleic acid;
wherein the first and second target nucleic acids comprise a plurality of regions of difference, the first and second subsets of oligonucleotide members correspond to the regions of difference, and the first and second subsets are present in substantially non-equimolar amounts; and,
wherein at least one variant member of the set of nucleic acids comprises a sequence which corresponds to the first target nucleic acid, the second target nucleic acid, or both the first and second target nucleic acid, which sequence comprises one or more sequence variation as compared to either the first or second target nucleic acid.

60. The composition of claim 59, wherein the variant member is selected from the group consisting of: a cross-over oligonucleotide, a codon-varied oligonucleotide, an oligonucleotide adjusted for codon bias, and a mutant oligonucleotide.

61. The composition of claim 1, wherein the set of nucleic acids comprises one or more cross-over oligonucleotide.

62. The composition of claim 61, wherein the first and second target nucleic acids display low sequence similarity.

63. The composition of claim 61, wherein the first and second target nucleic acids display low sequence similarity and wherein the cross-over oligonucleotide comprises a first subsequence corresponding to the first target nucleic acid and a second subsequence corresponding to the second target nucleic acid.

64. The composition of claim 1, wherein the first or second target nucleic acid are gene blended nucleic acids.

65. The composition of claim 1, wherein the first or second target nucleic acid comprise a frog gene or a human gene.

66. The composition of claim 1, wherein the first or second target nucleic acid encodes one or more of: erythropoietin, insulin, a peptide hormone, human growth hormone, a growth factor, a cytokine, epithelial Neutrophil Activating Peptide-78, GROα/MGSA, GROβ, GROγ, MIP-1α, MIP-16, MCP-1, epidermal growth factor, fibroblast growth factor, hepatocyte growth factor, insulin-like growth factor, an interferon, an interleukin, a keratinocyte growth factor, a leukemia inhibitory factor, oncostatin M, PD-ECSF, PDGF, pleiotropin, SCF, c-kit ligand, VEGEF, G-CSF, a transcriptional activator, an expression activator, an inflammatory molecule, a growth factor receptor, an oncogene product, IL-1, IL-2, IL-8, FGF, IGF-I, IGF-II, FGF, PDGF, TNF, TGF-cs, TGF-P, EGF, KGF, SCF/c-Kit, CD40L/CD40, VLA-4/VCAM-1, ICAM-1/LFA-1, hyalurin/CD44; Mos, Ras, Raf, Met, p53, Tat, Fos, Myc, Jun, Myb, Rel, a steroid hormone receptor, an Rnase, Onconase, EDN, a vaccine protein, a vaccine protein derived from an infectious fungus, a vaccine protein derived from a bacteria, a vaccine protein derived from a virus, an enzyme, a monooxygenase, a p450, a protease, a nuclease, a lipase, Alpha-I antitrypsin, Angiostatin, Antihemolytic factor, Apolipoprotein, Apoprotein, Atrial natriuretic factor, Atrial natriuretic polypeptide, an Atrial peptide, a C-X-C chemokines, T39765, NAP-2, ENA-78, Gro-a, Gro-b, Gro-c, IP-I0, GCP-2, NAP-4, SDF- 1, PF4, MIG), Calcitonin, a CC chemokine, Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, 1309, R83915, R91733, HCC1, T58847, D31065, T64262), CD40 ligand, Collagen, Colony stimulating fact (CSF), Complement factor 5*a*, Complement inhibitor, Complement receptor 1, Factor LX, Factor VII, Factor VIII, Factor X, Fibrinogen, Fibronectin, Glucocerebrosidase, Gonadotropin, a Hedgehog protein, Hemoglobin, Hirudin, Human serum albumin, Lactoferrin, Luciferase, Neurturin, Neutrophil inhibitory factor (NIF), Osteogenic protein, Parathyroid hormone, Protein A, Protein G, Relaxin, Renin, Salmon calcitonin, Salmon growth hormone, Soluble complement receptor I, Soluble I-CAM 1, a soluble interleukin receptor, a soluble TNF receptor, Somatomedin, Somatostatin, Somatotropin, Streptokinase, a Superantigen, a Staphylococcal enterotoxins, SEA, SEB, SEC1SEC2, SEC3, SED, SEE, Toxic shock syndrome toxin, exfoliating toxin A, exfoliating toxin B, Pyrogenic exotoxin A, Pyrogenic exotoxin B, Pyrogenic exotoxin C, M. arthritides mitogen, Superoxide dismutase, Thymosin alpha 1, Tissue plasminogen activator, Tumor necrosis factor beta (TNF beta), Tumor necrosis factor receptor (TNFR), Tumor necrosis factor-alpha (TNF alpha), Urokinase, a defensin, EF40, a peptide antibiotic, or a peptide insecticidal protein.

67. The composition of claim 1, wherein the first subset members comprise chemically synthesized oligonucleotides and the second subset members comprise chemically synthesized oligonucleotides.

68. The composition of claim 1, wherein the first subset members comprise a plurality of oligonucleotides of a selected length and the second subset members comprise a plurality of oligonucleotides of a selected length.

69. The composition of claim 25, wherein the first subset members comprise chemically synthesized oligonucleotides and the second subset members comprise chemically synthesized oligonucleotides.

70. The composition of claim 25, wherein the first subset members comprise a plurality of oligonucleotides of a selected length and the second subset members comprise a plurality of oligonucleotides of a selected length.

71. The method of claim 1, wherein the first subset collectively corresponds to 50% or more of the first target nucleic acid, or wherein the second subset collectively corresponds to 50% or more of the second target nucleic acid, or both.

72. The method of claim 1, wherein the first subset collectively corresponds to 60% or more of the first target nucleic acid, or wherein the second subset collectively corresponds to 60% or more of the second target nucleic acid, or both.

73. The method of claim 1, wherein the first subset collectively corresponds to 70% or more of the first target nucleic acid, or wherein the second subset collectively corresponds to 70% or more of the second target nucleic acird, or both.

74. The method of claim 1, wherein the first subset collectively corresponds to 80% or more of the first target nucleic acid, or wherein the second subset collectively corresponds to 80% or more of the second target nucleic acid, or both.

75. The method of claim 1, wherein the first subset collectively corresponds to 90% or more of the first target nucleic acid, or wherein the second subset collectively corresponds to 90% or more of the second target nucleic acid, or both.

76. The method of claim 1, wherein the first subset collectively corresponds to 100% of the first target nucleic acid, or wherein the second subset collectively corresponds to 100% of the second target nucleic acid, or both.

77. The method of claim 25, wherein the first subset collectively corresponds to 50% or more of the first target nucleic acid, or wherein the second subset collectively corresponds to 50% or more of the second target nucleic acid, or both.

78. The method of claim 25, wherein the first subset collectively corresponds to 60% or more of the first target nucleic acid, or wherein the second subset collectively corresponds to 60% or more of the second target nucleic acid, or both.

79. The method of claim 25, wherein the first subset collectively corresponds to 70% or more of the first target nucleic acid, or wherein the second subset collectively corresponds to 70% or more of the second target nucleic acid, or both.

80. The method of claim 25, wherein the first subset collectively corresponds to 80% or more of the first target nucleic acid, or wherein the second subset collectively corresponds to 80% or more of the second target nucleic acid, or both.

81. The method of claim 25, wherein the first subset collectively corresponds to 90% or more of the first target nucleic acid, or wherein the second subset collectively corresponds to 90% or more of the second target nucleic acid, or both.

82. The method of claim 25, wherein the first subset collectively corresponds to 100% of the first target nucleic acid, or wherein the second subset collectively corresponds to 100% of the second target nucleic acid, or both.

83. The composition of claim 49, wherein the first subset collectively corresponds to 50% or more of the first target nucleic acid, or wherein the second subset collectively corresponds to 50% or more of the second target nucleic acid, or both.

84. The composition of claim 49, wherein the first subset collectively corresponds to 60% or more of the first target nucleic acid, or wherein the second subset collectively corresponds to 60% or more of the second target nucleic acid, or both.

85. The composition of claim 49, wherein the first subset collectively corresponds to 70% or more of the first target nucleic acid, or wherein the second subset collectively corresponds to 70% or more of the second target nucleic acid, or both.

86. The composition of claim 49, wherein the first subset collectively corresponds to 80% or more of the first target nucleic acid, or wherein the second subset collectively corresponds to 80% or more of the second target nucleic acid, or both.

87. The composition of claim 49, wherein the first subset collectively corresponds to 90% or more of the first target nucleic acid, or wherein the second subset collectively corresponds to 90% or more of the second target nucleic acid, or both.

88. The composition of claim 49, wherein the first subset collectively corresponds to 100% of the first target nucleic acid, or wherein the second subset collectively corresponds to 100% of the second target nucleic acid, or both.

89. The composition of claim 59, wherein the first subset collectively corresponds to 50% or more of the first target nucleic acid, or wherein the second subset collectively corresponds to 50% or more of the second target nucleic acid, or both.

90. The composition of claim 59, wherein the first subset collectively corresponds to 60% or more of the first target nucleic acid, or wherein the second subset collectively corresponds to 60% or more of the second target nucleic acid, or both.

91. The composition of claim 59, wherein the first subset collectively corresponds to 70% or more of the first target nucleic acid, or wherein the second subset collectively corresponds to 70% or more of the second target nucleic acid, or both.

92. The composition of claim 59, wherein the first subset collectively corresponds to 80% or more of the first target nucleic acid, or wherein the second subset collectively correpsonds to 80% or more of the second target nucleic acid, or both.

93. The composition of claim 59, wherein the first subset collectively corresponds to 90% or more of the first target nucleic acid, or wherein the second subset collectively corresponds to 90% or more of the second target nucleic acid, or both.

94. The composition of claim 60, wherein the first subset collectively corresponds to 100% of the first target nucleic acid, or wherein the second subset collectively corresponds to 100% of the second target nucleic acid, or both.

* * * * *